United States Patent
Miyadera et al.

(10) Patent No.: US 8,564,781 B2
(45) Date of Patent: Oct. 22, 2013

(54) SPR SENSOR

(75) Inventors: Nobuo Miyadera, Ushiku (JP); Kenta Mizusawa, Jyouetsu (JP); Kazunari Shinbo, Niigata (JP); Yasuo Ohdaira, Niigata (JP); Akira Baba, Niigata (JP); Keizo Kato, Niigata (JP); Futao Kaneko, Niigata (JP); Takahiro Kawakami, Tsubame (JP)

(73) Assignees: Hitachi Chemical Company, Ltd., Tokyo (JP); Niigata University, Niigata (JP)

( * ) Notice: Subject to any disclaimer, the term of this patent is extended or adjusted under 35 U.S.C. 154(b) by 90 days.

(21) Appl. No.: 13/061,620

(22) PCT Filed: Aug. 21, 2009

(86) PCT No.: PCT/JP2009/064662
§ 371 (c)(1),
(2), (4) Date: Mar. 1, 2011

(87) PCT Pub. No.: WO2010/024202
PCT Pub. Date: Mar. 4, 2010

(65) Prior Publication Data
US 2011/0157593 A1 Jun. 30, 2011

(30) Foreign Application Priority Data
Sep. 1, 2008 (JP) ................................. 2008-224114

(51) Int. Cl.
*G01N 21/55* (2006.01)
(52) U.S. Cl.
USPC ........................................................ 356/445
(58) Field of Classification Search
USPC ............... 356/445–448, 246, 244; 250/459.1, 250/458.1, 576; 436/171, 172, 501
See application file for complete search history.

(56) References Cited

U.S. PATENT DOCUMENTS

| 5,313,264 A * | 5/1994 | Ivarsson et al. ................. 356/73 |
| 7,692,795 B2 * | 4/2010 | Sasaki et al. .................. 356/445 |

(Continued)

FOREIGN PATENT DOCUMENTS

| JP | 2001-041881 | 2/2001 |
| JP | 2001-337036 | 12/2001 |
| JP | 2002-162346 | 6/2002 |
| JP | 2003-294610 | 10/2003 |
| JP | 2007-263736 | 10/2007 |
| WO | WO 2005/054826 A1 | 6/2005 |
| WO | WO 2008/075578 A1 | 6/2008 |

OTHER PUBLICATIONS

Translation of the International Preliminary Report dated Apr. 21, 2011.

(Continued)

*Primary Examiner* — Sang Nguyen
(74) *Attorney, Agent, or Firm* — Antonelli, Terry, Stout & Kraus, LLP.

(57) ABSTRACT

Provided is an SPR sensor which can achieve compaction and multichannel detection by simple configuration at a low cost. The SPR sensor comprises an optical path, and detection areas on the side surface thereof formed by laminating metal layers formed to cause surface plasmon resonance phenomenon. The SPR sensor is characterized in that two or more detection areas are formed for one optical path, a dielectric constant regulation layer is further laminated in at least one of the two or more detection areas, dielectric constant is regulated to have a different surface plasmon resonance in each detection area, and a dielectric constant regulation layer laminated in the at least one of the two or more detection areas functions as a layer exhibiting sensitivity to an object to be detected.

28 Claims, 27 Drawing Sheets

(56) References Cited

U.S. PATENT DOCUMENTS

| | | | |
|---|---|---|---|
| 7,999,941 B2* | 8/2011 | Matsushita et al. | 356/445 |
| 2004/0141300 A1* | 7/2004 | Takubo et al. | 362/5 |
| 2007/0211254 A1* | 9/2007 | Matsushita et al. | 356/445 |
| 2008/0218761 A1* | 9/2008 | Nishikawa et al. | 356/445 |
| 2009/0086210 A1* | 4/2009 | Ho et al. | 356/445 |
| 2009/0128822 A1* | 5/2009 | Yamamichi et al. | 356/445 |
| 2009/0321661 A1* | 12/2009 | Ohtsuka | 250/459.1 |
| 2009/0325315 A1* | 12/2009 | Hirai et al. | 436/501 |

OTHER PUBLICATIONS

Yutaka Kobayashi et al., Humidity Sensing Using Surface Plasmon Excitation in Fluorescent Microsphere Films, Transactions of the Materials Research Society of Japan, 2007, pp. 317-320, vol. 32, No. 2.

Japanese Official Action dated Apr. 16, 2013, for JP Application No. 201-526685.

* cited by examiner

FIG. 10
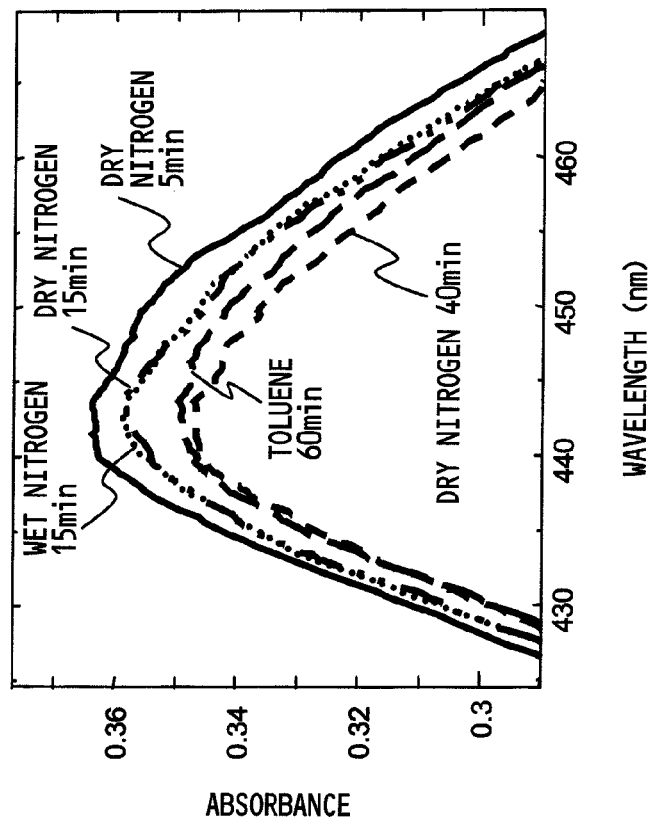
(b) LONG-WAVELENGTH SIDE
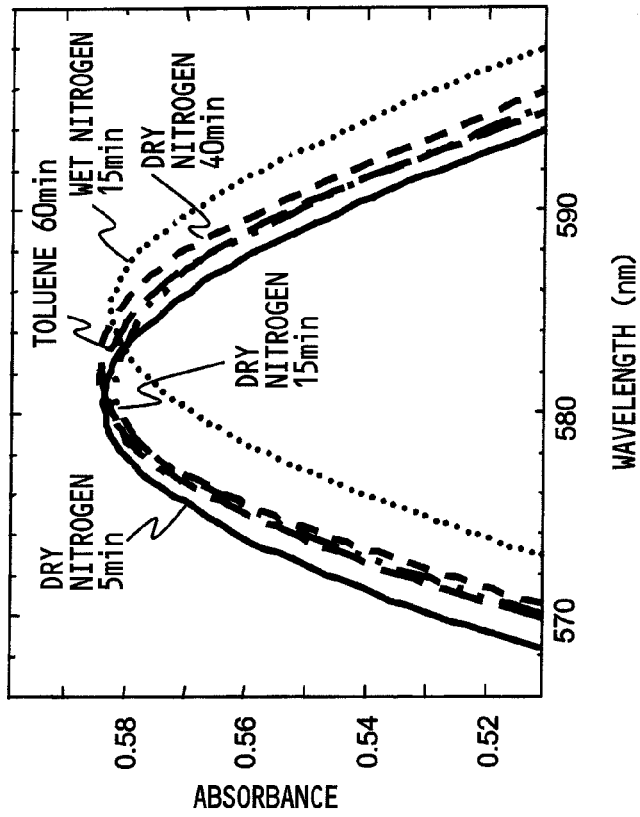
(a) SHORT-WAVELENGTH SIDE

SPR SENSOR

TECHNICAL FIELD

The present invention relates to a sensor utilizing a surface plasmon resonance (SPR) phenomenon. More specifically, the present invention relates to an SPR sensor capable of simultaneously detecting two or more objects to be detected.

BACKGROUND ART

As a sensor capable of performing qualitative/quantitative analysis of an object to be detected with high sensitivity, an SPR sensor utilizing a surface plasmon resonance phenomenon has been proposed and practically used.

As one example of a known structure of such an SPR sensor, there is a structure in which light emitted from a light source is allowed to enter the incidence plane of a high refractive index prism, which has a metal thin film on its plane different from the incident plane, at a predetermined incident angle so that the metal thin film being in contact with an object to be detected is irradiated with the light, and light produced by reflection at the boundary between the prism and the metal thin film is allowed to exit the prism through another plane to detect a change in the intensity of the output light by a detector. In the case of such a structure, light emitted from the light source and then entering the prism produces an evanescent wave at the boundary between the prism and the metal thin film, and on the other hand, a surface plasmon wave is produced at the surface of the metal thin film. The surface plasmon wave is produced (excited) when the incident angle of light or the wavelength of incident light is adjusted so that the wave number of the evanescent wave becomes equal to the wave number of the surface plasmon wave, and at this time the energy of incident light is used to excite the surface plasmon wave and therefore the intensity of reflected light is attenuated. The thickness and refractive index of an object to be detected can be determined from a relationship between the intensity of reflected light and the wavelength at which the intensity of reflected light is attenuated, and the qualitative/quantitative analysis of the object to be detected can be performed using the thus determined refractive index.

In recent years, there has been an increasing demand for an SPR sensor capable of achieving miniaturization and multichannel detection. However, an SPR sensor having the above-described structure using a prism has a problem that its size is large, and even when such an SPR sensor is configured to achieve multichannel detection, its size is further increased. For this reason, it is difficult for such an SPR sensor to achieve both miniaturization and multichannel detection.

On the other hand, an optical waveguide-type SPR sensor using an optical waveguide has been proposed (see, for example, Patent Document 1). Such an optical waveguide-type SPR sensor generally includes an optical waveguide having a core and a cladding surrounding the core and a sensor unit provided by exposing the core through an opening formed in part of the cladding and fixing a metal thin film on at least part of the exposed core so that the metal thin film comes into contact with the exposed core. When such an optical waveguide-type SPR sensor is used to detect an object to be detected, the object to be detected is brought into contact with the sensor unit. Such an optical waveguide-type SPR sensor does not require a prism and therefore can be reduced in size. Further, such an optical waveguide-type SPR sensor can achieve multichannel detection by providing two or more cores (sensor units).

Further, Patent Document 2 proposes an optical waveguide-type SPR sensor including a sensor array unit which is composed of plural waveguides in parallel, each of which is arranged with a metal thin film as a waveguide-type SPR sensor, where the metal films are different in dielectric constant and/or film thickness from each other. Such an optical waveguide-type SPR sensor makes it possible to perform high-resolution and high-sensitive multichannel detection over a wide refractive index range.

Further, Patent Document 3 proposes an optical waveguide-type SPR sensor for multichannel detection including a waveguide unit having two or more cores and a switching unit having two or more switching elements each of which is capable of performing switching between a state where an objected to be measured is detected and a state where an object to be measured is not detected, wherein the switching unit is stacked on the waveguide unit so that the switching elements are arranged along the length direction of the cores. Such an optical waveguide-type SPR sensor can achieve certain results from the viewpoint of miniaturization and multichannel detection. However, such an optical waveguide-type SPR sensor requires two or more switching devices and therefore has a complicated structure, and in addition, it is difficult to produce such an optical waveguide-type SPR sensor at low cost.

The above-described optical waveguide-type SPR sensors can be made smaller in size as compared to an SPR sensor using a prism. However, each of these optical waveguide-type SPR sensors requires an array of two or more optical paths or a switching mechanism to achieve multichannel detection, which limits reduction in size. Further, it is difficult to produce these optical waveguide-type SPR sensors at low cost.

PRIOR ART DOCUMENTS

Patent Documents

Patent Document 1: JP-A No. 2002-162346
Patent Document 2: JP-A No. 2007-263736
Patent Document 3: WO 2005/054826

SUMMARY OF THE INVENTION

Technical Problems

The present invention has been made in view of the foregoing problems, and an object of the present invention is to provide an SPR sensor capable of achieving miniaturization and multichannel detection by a simple structure at a low cost.

Solution to the Problems

In order to achieve the above object, the present invention provides the following means.
(1) An SPR sensor including:
an optical path; and
detection regions provided by laminating, on one side surface or plural side surfaces of the optical path, metal layers formed so as to cause a surface plasmon resonance phenomenon, wherein the detection regions are provided at two or more positions on one optical path, and wherein a dielectric constant regulation layer is further laminated in at least one of the two or more detection regions and a dielectric constant of the dielectric constant regulation layer is regulated so that the two or more detection regions have different surface plasmon resonances, and wherein the dielectric constant regulation layer laminated in at least one of the two or more detection regions functions as a sensitive layer having sensitivity to an object to be detected.

(2) The SPR sensor according to the above (1), wherein at least one of the two or more detection regions is composed of only a metal layer formed so as to cause a surface plasmon resonance phenomenon and at least one of the two or more detection regions which is different from the detection region composed of only a metal layer is composed of a metal layer formed so as to cause a surface plasmon resonance phenomenon and a dielectric constant regulation layer laminated on the metal layer.

(3) The SPR sensor according to the above (1), wherein each of the detection regions is composed of a metal layer formed so as to cause a surface plasmon resonance phenomenon and a dielectric constant regulation layer laminated on the metal layer, and wherein the detection regions are provided at two or more positions on one optical path, and wherein a dielectric constant of each of the dielectric constant regulation layers laminated in the two or more detection regions is regulated so that the two or more detection regions have different surface plasmon resonances, and wherein the dielectric constant regulation layer laminated in at least one of the two or more detection regions functions as a sensitive layer having sensitivity to an object to be detected.

(4) The SPR sensor according to any one of the above (1) to (3), wherein each of the two or more detection regions has a dielectric constant regulation layer laminated therein, and the dielectric constant regulation layers provided in the two or more detection regions function as sensitive layers having sensitivity to different objects to be detected.

(5) The SPR sensor according to any one of the above (1) to (3), wherein each of the two or more detection regions has a dielectric constant regulation layer laminated therein, and the dielectric contact regulation layers provided in the two or more detection regions are made of different materials.

(6) The SPR sensor according to any one of the above (1) to (3), wherein a dielectric constant regulation layer that functions as an insensitive layer not having sensitivity to an object to be detected is laminated in at least one of the two or more detection regions which is different from the detection region in which a dielectric constant regulation layer that functions as a sensitive layer having sensitivity to an object to be detected is laminated.

(7) The SPR sensor according to any one of the above (1) to (3), wherein when detection is performed using an optical path having two or more detection regions, a p-polarization component is used as detection light and an s-polarization component is used as reference light.

(8) The SPR sensor according to any one of the above (1) to (3), wherein the dielectric constant regulation layers are different in thickness between the detection regions.

(9) The SPR sensor according to any one of the above (1) to (3), wherein the dielectric constant regulation layer is made of a transparent medium.

(10) The SPR sensor according to any one of the above (1) to (3), wherein the optical path is located in a transparent substrate.

(11) The SPR sensor according to the above (10), wherein the transparent substrate is made of inorganic glass.

(12) The SPR sensor according to the above (10), wherein the transparent substrate is made of a polymer.

(13) The SPR sensor according to any one of the above (1) to (3), wherein the optical path is part of a core layer of a two-dimensional optical waveguide.

(14) The SPR sensor according to any one of the above (1) to (3), wherein the optical path is a core of a three-dimensional optical waveguide.

(15) The SPR sensor according to any one of the above (1) to (3), wherein the optical path is a core of an optical fiber.

(16) The SPR sensor according to any one of the above (1) to (3), wherein the metal layer is made of at least one metal selected from the group consisting of Au, Ag, Pt, Cu, and Al.

(17) The SPR sensor according to any one of the above (1) to (3), wherein the sensitive layer contains a solvent-soluble material as a material having sensitivity.

(18) The SPR sensor according to the above (17), wherein the solvent-soluble material is a hydrophilic material.

(19) The SPR sensor according to the above (18), wherein the hydrophilic material is at least one selected from the group consisting of polyvinyl alcohol, polyacrylic acid, polystyrene sulfonic acid, polyallylamine, poly(diallyldimethylammonium chloride), polyamide acid, and polyimide precursors.

(20) The SPR sensor according to the above (17), wherein the solvent-soluble material is a hydrophobic material.

(21) The SPR sensor according to the above (20), wherein the hydrophobic material is polyvinylcarbazole, polymethylmethacrylate, wax, polyimide, or polytetrafluoroethylene.

(22) The SPR sensor according to any one of the above (1) to (3), wherein the sensitive layer contains a material having sensitivity with a polymer as a matrix.

(23) The SPR sensor according to any one of the above (6), wherein the insensitive layer is made of one material selected from the group consisting of glass films, alkali-free glass films, silicon oxide films, quartz glass films, magnesium fluoride films, alumina films, titania films, silicon nitride films, and ITO films.

Advantageous Effects of the Invention

According to the present invention, it is possible to provide an SPR sensor capable of achieving miniaturization and multichannel detection by a simple structure at a low cost.

BRIEF DESCRIPTION OF THE DRAWINGS

FIG. 10(a) is an enlarged view of the absorption spectra shown in FIG. 9, which shows absorption peaks on the short-wavelength side.

FIG. 10(b) is an enlarged view of the absorption spectra shown in FIG. 9, which shows absorption peaks on the long-wavelength side.

DESCRIPTION OF EMBODIMENTS

An SPR sensor according to the present invention comprises an optical path and detection regions provided by laminating, on a side surface of the optical path, metal layers formed to cause a surface plasmon resonance phenomenon, wherein the detection regions are provided at two or more positions on one optical path, and wherein a dielectric constant regulation layer is further laminated in at least one of the two or more detection regions and a dielectric constant of the dielectric constant regulation layer is regulated so that the two or more detection regions have different surface plasmon resonances, and wherein the dielectric constant regulation layer laminated in at least one of the two or more detection regions functions as a sensitive layer having sensitivity to an object to be detected.

That is, the SPR sensor according to the present invention allows two or more detection regions to be provided for one optical path, and therefore can achieve both miniaturization and multichannel detection. Further, the SPR sensor according to the present invention does not require a mechanism such as a switching device, and therefore can be produced at a low cost.

More specifically, the SPR sensor according to the present invention is configured to have two or more detection regions arranged along the length direction of one optical path (i.e., along the direction in which detection light travels) so that detection signals can be measured by the two or more detection regions at different wavelengths. Therefore, as compared to a conventional method in which only one detection signal can be measured per one optical path, the SPR sensor according to the present invention can be more easily integrated into a device and the device can be miniaturized because detection signals measured by the two or more detection regions are multiplexed and the multiplexed detection signals can be easily separated from each other. Further, unlike a conventional case where two or more optical paths are provided in parallel, the SPR sensor according to the present invention allows two or more detection signals to be obtained by one common optical path, and therefore there is little possibility that deviations from desired (designed) characteristics occur due to manufacturing variations between different optical paths, and manufacturing tolerances are large and thus manufacturing costs can be reduced.

Hereinafter, the SPR sensor according to the present invention will be described in detail.

Figure 1:
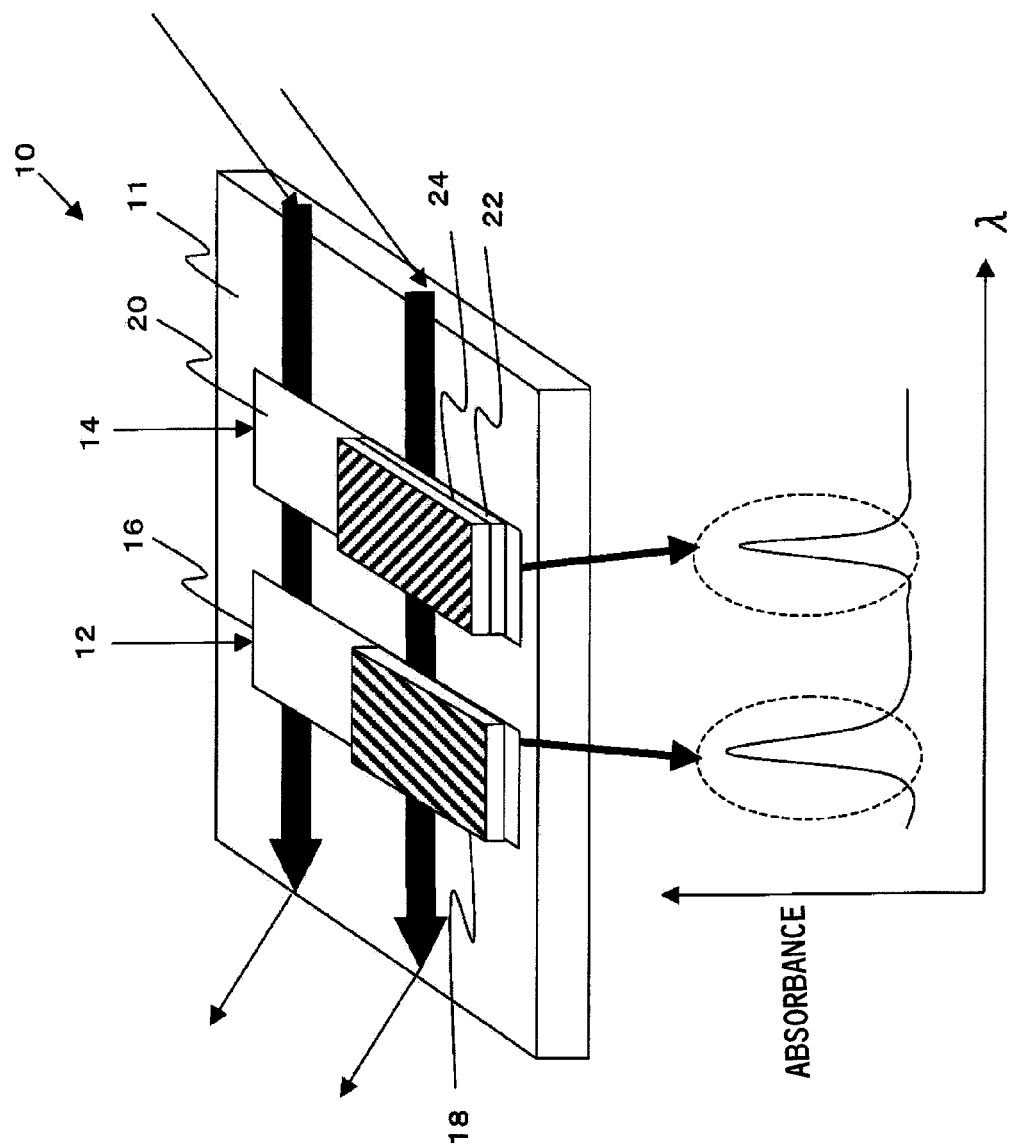
FIG. 1 is a schematic perspective view of one example of an SPR sensor according to the present invention.

FIG. 1 is a diagram showing one embodiment of the SPR sensor according to the present invention.

An SPR sensor 10 shown in FIG. 1 includes a slide glass (transparent substrate) 11 and two detection regions 12 and 14 provided on the slide glass 11. In one of the detection regions 12, a metal layer 16 made of Ag and a PVK (polyvinylcarbazole) layer 18 formed on the metal layer 16 as a dielectric constant regulation layer (sensitive layer) are provided. In the other detection region 14, a metal layer 20 and a MgF$_2$ (magnesium fluoride) layer 22 and a PVA (polyvinyl alcohol) layer 24 laminated in this order on the metal layer 20 as dielectric constant regulation layers are provided. The dielectric constant of the PVK layer 18, which is a dielectric constant regulation layer, and the dielectric constant of the MgF$_2$ layer 22 and the PVA layer 24, which are dielectric constant regulation layers, are regulated so that the detection regions 12 and 14 have different surface plasmon resonances. The PVK layer 18 and the PVA layer 24 provided in the detection regions 12 and 14, respectively, are made of different materials, and function as a sensitive layer having sensitivity to a hydrophobic material and a sensitive layer having sensitivity to a hydrophilic material, respectively.

On the other hand, in each of the detection regions, the metal layer is exposed without providing any layer thereon in a region where no dielectric constant regulation layer is provided. The SPR sensor 10 has an optical path through which light propagates while being reflected at a region where the dielectric constant regulation layer(s) is(are) provided in each of the detection regions and an optical path through which light propagates while being reflected at a region where no dielectric constant regulation layer is provided in each of the detection regions. The former is used as an optical path for detection and the latter is used as an optical path for reference light. Alternatively, an optical path through which light propagates while being reflected at a region where neither metal layer nor dielectric constant regulation layer is provided may be provided to be used as an optical path for reference light. It is to be noted that, each of the optical paths provided in the SPR sensor shown in FIG. 1 is a region where light having a width of about the thickness of the slide glass 11 propagates in the direction of group velocity in part of the slide glass 11, and is located on the side surface of the metal layer 16. However, it is difficult to draw a concrete region of each of the optical paths, and therefore each of the optical paths is conceptually represented by a thick arrow in FIG. 1, which suggests that when the propagation of light through each of the optical paths is geometric-optically illustrated using a plane-wave beam, the plane-wave beam can be represented by a zigzag line.

The incident angle of light that enters and then propagates through each of the optical paths is set so that the light is totally reflected at the detection regions.

When detection is performed using the SPR sensor 10 shown in FIG. 1, incident light enters the right-side end face of the slide glass 11, propagates through the optical path while being totally reflected at the two detection regions 14 and 12, and exits from the left-side end face of the slide glass 11 (see the arrow shown in FIG. 1). At this time, a surface plasmon resonance phenomenon occurs at the two detection regions 14 and 12, and therefore the intensity of reflected light obtained by total reflection at one of the detection regions and the intensity of reflected light obtained by total reflection at the other detection region are reduced at different wavelengths, and the refractive indexes of objects to be detected can be determined from these wavelengths. It is to be noted that an absorption spectrum shown below the SPR sensor 10 in FIG. 1 indicates that the wavelength of an absorption peak detected by one of the detection regions and the wavelength of an absorption peak detected by the other detection region are different. In the present invention, the dielectric constant of the dielectric constant regulation layer provided in each of the detection regions is regulated so that the detection regions have different surface plasmon resonances. This is because absorption peaks detected by different detection regions can be easily distinguished from each other by allowing absorption peaks to be detected by the detection regions at different wavelengths. This point will be described later.

On the other hand, light that propagates through the optical path for reference light is reflected at a region where the metal layer is provided in each of the detection regions and exits from an outlet. The spectrum of reference light is used as a reference against the spectrum of an object to be detected. Alternatively, an optical path through which light propagates while being reflected at a region where neither metal layer nor dielectric constant regulation layer is provided may be provided in order to use the spectrum of light that exits from such an optical path as a reference against the spectrum of an object to be detected.

Although not shown concretely in the drawings, unlike the above-mentioned example where an optical path for reference light is separately provided, a reference region may be provided on the side surface of one common optical path separately from the detection regions. This structure also makes it possible to obtain the effects of the present invention, that is, to reduce the number of channels provided in parallel as well as to avoid performance variations between adjacent optical paths resulting from manufacturing variations.

Figure 2:
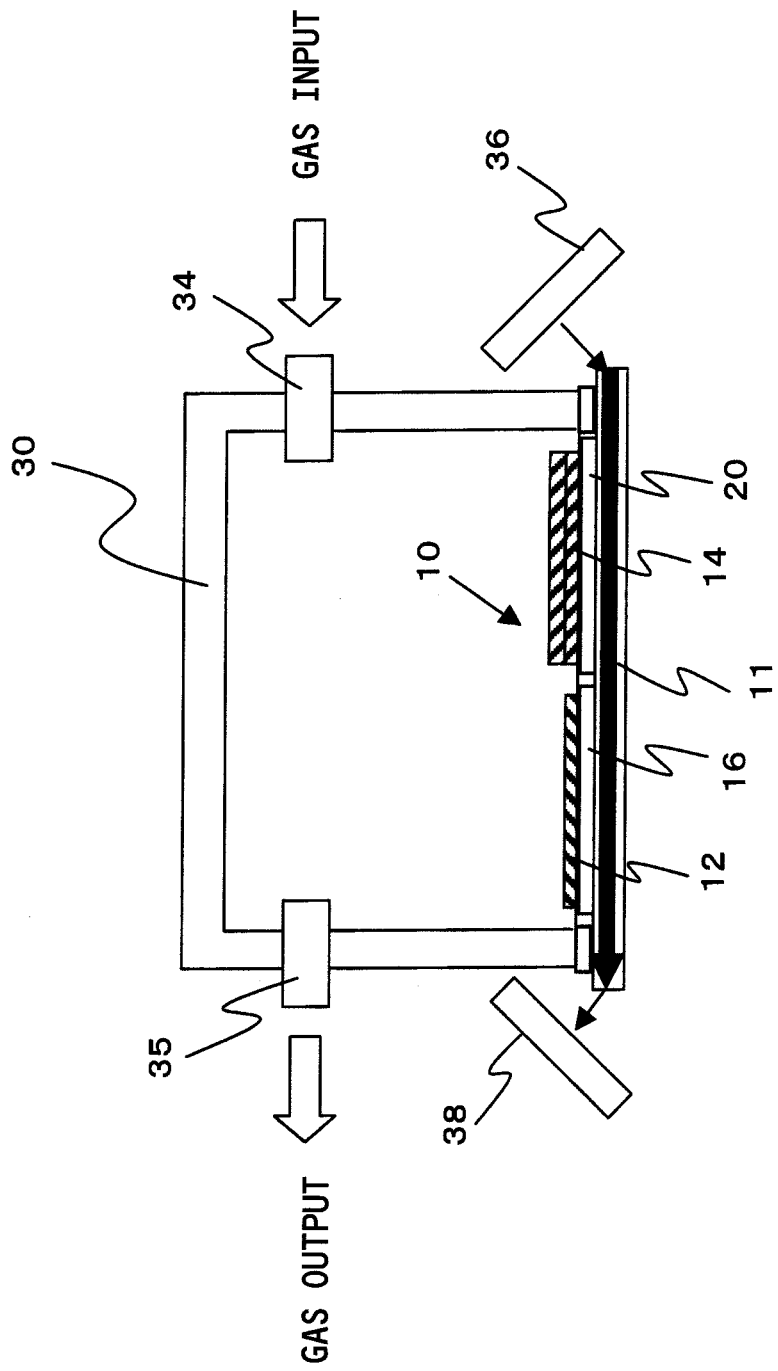
FIG. 2 is a schematic view of a gas detection device using the SPR sensor according to the present invention.

FIG. 2 is a schematic view showing the structure of a gas detection device using the SPR sensor shown in FIG. 1. As shown in FIG. 2, a casing 30 is provided so as to cover the SPR sensor 10, and has a gas inlet 34 through which a gas is introduced and a gas outlet 35 through which a gas is discharged. A gas introduced through the gas inlet 34 flows through the internal space of the casing 30 serving as a gas flow path, and part of the gas supplied to the internal space of the casing 30 is brought into contact with (adsorbed to) the detection regions of the SPR sensor and used for detection, and the remaining gas is discharged through the gas outlet 35.

On the other hand, as shown in FIG. 2, a light source 36 is provided on the right side of the casing 30 (SPR sensor 10), and a detector 38 is provided on the left side of the casing 30. Light emitted from the light source 36 enters the right-side end face of the SPR sensor 10, propagates through the optical path provided in the slide glass 11, exits from the left-side end face of the SPR sensor 10, and reaches the detector 38, and then, for example, light intensity is detected by the detector 38. Although not shown in FIG. 2, the detector 38 is connected to an arithmetical unit such as a computer, and arithmetic processing is performed by the arithmetical unit based on detected data of light intensity.

The detection device shown in FIG. 2 uses the SPR sensor having two types of sensitive layers, that is, a sensitive layer having sensitivity to a hydrophobic material and a sensitive layer having sensitivity to a hydrophilic material, and therefore, as described above, can easily detect a hydrophilic gas and a hydrophobic gas.

Hereinafter, the detection principles of the SPR sensor according to the present invention will be described. When light that has entered the optical path through its inlet reaches the surface of the metal layer of the detection region having the structure described above and is totally reflected, an evanescent wave is produced at the interface between the optical path and the metal layer, and penetrates into an object to be detected present on the surface of the detection region. The wave number of the evanescent wave is determined by the frequency and propagation angle of light propagating through the optical path. Further, a surface plasmon wave can be excited at the surface of the metal layer by this evanescent wave, and the wave number of this surface plasmon wave is determined by the film thickness and refractive index of the object to be detected and the film thickness and refractive index of a metal constituting the metal layer.

When the wave number of an evanescent wave and the wave number of a surface plasmon wave are the same, as described above, the evanescent wave is used as light required to excite the surface plasmon wave so that the intensity of reflected light is attenuated. Therefore, by monitoring the intensity and wavelength of reflected light (i.e., output light), the refractive index and thickness of an object to be detected can be determined from the wavelength (reciprocal of wave number) of reflected light at which the intensity of the output light is attenuated. It is to be noted that surface plasmon is excited by a so-called p-polarization component (in FIG. 2, a polarized wave having an electric field component parallel to the plane of paper). In a case where the dielectric constant regulation layer is sufficiently thick, the SPR sensor can operate as an optical waveguide mode sensor that determines the refractive index and thickness of an object to be detected by measuring the attenuation of output light caused by a waveguide mode excited when the dielectric constant regulation layer satisfies waveguide conditions. The waveguide mode can be excited by either a p- or s-polarization component.

As described above, the SPR sensor according to the present invention allows two or more detection regions to be provided for one optical path to simultaneously detect two or more objects to be detected present on these detection regions. However, it is difficult to simultaneously detect two or more objects to be detected by simply providing the same detection regions at two or more positions, because absorption peaks overlap each other. Therefore, in the present invention, different detection regions are allowed to have different absorption peak wavelengths, which makes it possible to perform simultaneous detection. More specifically, in a case where two detection regions are provided, the absorption peak wavelengths of the two detection regions are set so that two absorption peaks appear on the long-wavelength and short-wavelength sides to distinguish the two absorption peaks from each other, which makes it possible to perform detection by two detection regions. Also in a case where three or more detection regions are provided for one optical path, three or more objects to be detected can be simultaneously detected by providing three or more detection regions on one optical path and setting the prescribed absorption peak wavelengths to each detection region.

Examples of a method for allowing different detection regions to have different absorption peak wavelengths include: (1) changing the material of the dielectric constant regulation layer between the detection regions; (2) changing the thickness of the dielectric constant regulation layer between the detection regions; and (3) changing the type of metal used for forming the metal layer between the detection regions. These methods (1) to (3) may be used in combination of two or more of them.

On the other hand, in a case where the difference between the absorption peak wavelengths of the detection regions, which are made different from each other in such a manner as described above, is less than a certain level so that adjacent absorption peaks are close to each other, the half-width of a resonance absorption band is preferably made small to prevent crosstalk. The half-width of a resonance absorption band is preferably made small by, for example, reducing the thickness of the dielectric constant regulation layer and using a high dielectric constant material as a constituent material of the dielectric constant regulation layer.

Figure 16:
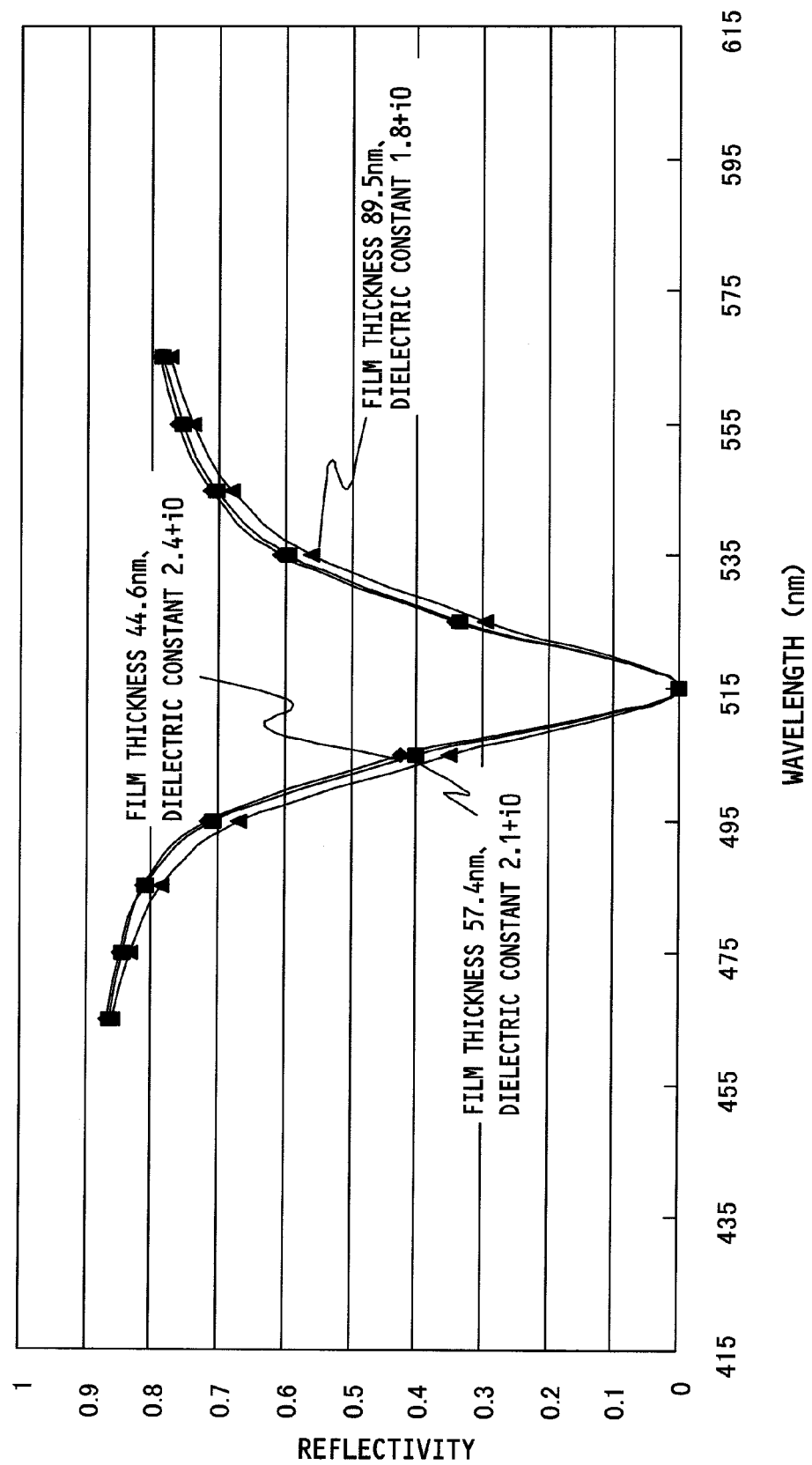
FIG. 16 is a graph showing the reflectivity spectra of three detection regions of the SPR sensor according to the present invention different in the thickness and dielectric constant of a dielectric constant regulation layer from one another, which were measured using light having a wavelength of 515 nm.
Figure 17:
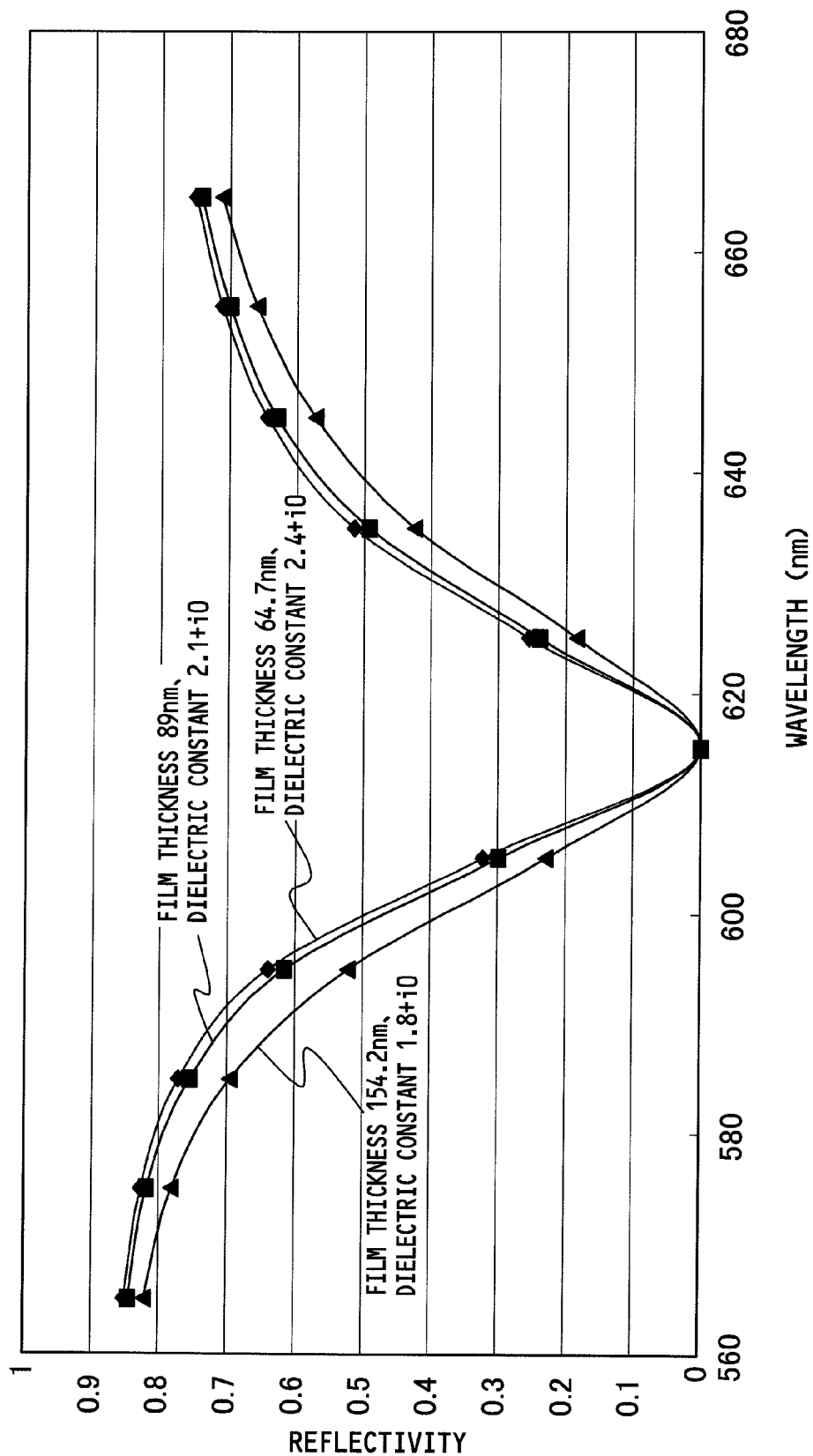
FIG. 17 is a graph showing the reflectivity spectra of three detection regions of the SPR sensor according to the present invention different in the thickness and dielectric constant of a dielectric constant regulation layer from one another, which were measured using light having a wavelength of 615 nm.

FIG. 16 shows the reflectivity spectra of three detection regions different in the thickness and dielectric constant of a dielectric constant regulation layer from one another, which were measured using light having a wavelength of 515 nm, and FIG. 17 shows the reflectivity spectra of three detection regions different in the thickness and dielectric constant of a dielectric constant regulation layer from one another, which were measured using light having a wavelength of 615 nm. These reflectivity spectra are based on calculation results obtained by allowing light to enter a structure, in which a silver thin film and a dielectric thin film are laminated on a rectangular plane of a half-cylindrical prism (material: BK-7), at an incident angle of 65°. The dielectric constant of the silver thin film at each wavelength was determined from Drude's model and the calculation was done using a transfer matrix method. As can be seen from FIGS. 16 and 17, when the thickness and dielectric constant of the dielectric constant regulation layer are 44.6 nm and 2.4+i0, respectively and the thickness and dielectric constant of the dielectric constant regulation layer are 67.4 nm and 2.4+i0, respectively, that is, when the thickness of the dielectric constant regulation layer is the smallest and the dielectric constant of the dielectric constant regulation layer is the highest, the half-width of a resonance absorption band is the smallest. This suggests that the half-width of a resonance absorption band can be made smaller by reducing the thickness of the dielectric constant regulation layer and using a material having a higher dielectric constant as a constituent material of the dielectric constant regulation layer. More specifically, the thickness of the dielectric constant regulation layer is preferably 1 to 200 nm, more preferably 20 to 100 nm. Further, the dielectric constant of the dielectric constant regulation layer having a thickness within the above range is preferably 1.2 to 4, more preferably 1.5 to 3.

Hereinafter, components constituting the SPR sensor according to the present invention will be described.

As a material of the transparent substrate, inorganic glass or a polymer can be used. The use of inorganic glass makes it possible to reduce the effect of absorption of a specimen (object to be detected) into the substrate on detection characteristics. Examples of the polymer include polymethylmethacrylate and polyethylene terephthalate. Among them, polymethylmethacrylate is preferred.

The thickness of the transparent substrate is preferably 0.01 to 2.0 mm.

Examples of the optical path include part of a core layer of a two-dimensional optical waveguide, a three-dimensional optical waveguide core, and an optical fiber core.

A two-dimensional optical waveguide can be easily produced, but lateral optical confinement is slightly weak, and therefore incident light needs to be chosen (e.g., parallel beam). On the other hand, a three-dimensional optical waveguide exhibits less loss, and therefore detection sensitivity can be improved. An optical fiber allows remote detection.

In the case of a two-dimensional optical waveguide, detection regions can be arranged with high area efficiency by providing an optical path in a zigzag manner by, for example, setting optical paths in two different directions such as from left to right and from top to bottom, or by allowing detection light to be reflected at the end of the two-dimensional optical waveguide. On the other hand, in the case of a three-dimensional optical waveguide, detection signals can be outputted from their respective appropriate positions by bending or branching the optical waveguide, and in addition, sensitivity can be improved and spectroscopic function can be easily imparted to the SPR sensor by integration with well-known optical waveguide-type devices such as MZ interferometer or AWG. For example, in the case of the present invention, after detection light is allowed to pass through two or more detection regions provided on a three-dimensional optical waveguide used as an optical path, a wavelength spectrum can be directly obtained by demultiplexing two or more detection signals by an AWG and outputting them to different output ports or by guiding two or more detection signals to an array-type photodetector provided at the end of the optical waveguide. This makes it possible to eliminate the necessity to externally provide a spectrometer and thereby to omit a component such as a prism or a grating, which allows miniaturization of the SPR sensor.

Further, in the case of a two-dimensional optical waveguide, an optical path is composed of part of a core of the two-dimensional optical waveguide and a cladding surrounding the core. That is, in the case of a two-dimensional optical waveguide (slab film), an optical path is only part of a core layer through which light passes. Therefore, in a case where the SPR sensor according to the present invention uses a two-dimensional optical waveguide as an optical path, unlike the above-described SPR sensors utilizing a three-dimensional optical waveguide disclosed in JP-A No. 2007-263736 and JP-A No. 2002-162346, two or more detection regions arranged in substantially a matrix in a plane can be provided on the side surface of one optical path by, for example, setting a two-dimensional optical waveguide so that its optical path becomes not a simple straight line but a reciprocating zigzag line. On the other hand, in the case of the SPR sensor disclosed in JP-A No. 2007-263736, two or more optical waveguides are arranged in a parallel array to provide two or more detection regions so that the detection regions are separated from each other, but this is based on the premise that the optical waveguides are three-dimensional optical waveguides. Therefore, in this case, in order to arrange two or more detection regions in a matrix, it is necessary to perform switching between optical paths by a mechanism such as a switch from measurement to measurement. However, the SPR sensor according to the present invention can eliminate such a necessity and therefore can achieve miniaturization.

The detection region is provided by a metal layer or a laminated structure of a metal layer and a dielectric constant regulation layer (sensitive layer). In either case, the detection region is provided on the side surface of the optical path. It is to be noted that in a case where the optical path is an optical waveguide or an optical fiber, the optical path sometimes refers to a portion including both a core and a cladding. This means that an optical wave propagating through the optical path is not spatially confined only within a core but penetrates as an evanescent field into a cladding. In the present invention, the "optical path" in the phrase "side surface of the optical path (on which detection regions are provided)" is used for the purpose of achieving surface plasmon resonance and therefore refers to about a portion from which the evanescent wave leaks and penetrates into the metal film, the dielectric constant regulation layer, the sensitive layer, and the insensitive layer provided on the side surface thereof. Therefore, the "optical path" may refer to either only a core or a portion including a core and a cladding for regulating optical waveguiding which is thinner than usual.

The metal layer is preferably made of at least one metal selected from the group consisting of Au, Ag, Pt, Cu, and Al. The metal layer may be a single layer made of one metal or an alloy multilayer film made of two or more different metals.

It is to be noted that the optimum thickness of the metal layer varies depending on the type of metal used or the complex dielectric constant of the dielectric constant regulation layer, and therefore the thickness of the metal layer is preferably selected according to desired detection sensitivity. For example, in the case of Au, the thickness of the metal layer is preferably selected in the range of about 40 nm±10 nm, and in the case of Ag.Cu, the thickness of the metal layer is preferably selected in the range of about 50 nm±10 nm, and in the case of Al.Pt, the thickness of the metal layer is preferably selected in the range of 15 nm±10 nm.

The metal layer can be formed by sputtering, vacuum vapor deposition, or the like.

In a case where different detection regions are allowed to have different absorption peak wavelengths by changing the type of metal used for forming the metal layer, a combination of metals used for different metal layers is preferably, for example, a combination of metals with a relatively large difference in dielectric constant such as a combination of Au and Ag.

In the present invention, as described above, a dielectric constant regulation layer is further laminated in at least one of the two or more detection regions, and the dielectric constant of the dielectric constant regulation layer is regulated so that the detection regions have different surface plasmon resonances, and the dielectric constant regulation layer laminated in at least one of the two or more detection regions functions as a sensitive layer having sensitivity to an object to be detected.

Alternatively, at least one of the two or more detection regions may be configured as a detection region composed of a metal layer formed to cause a surface plasmon resonance phenomenon and at least one of the two or more detection regions different from the detection region composed of a metal layer may be configured as a detection region composed of a metal layer formed to cause a surface plasmon resonance phenomenon and a dielectric constant regulation layer laminated on the metal layer.

Alternatively, two or more detection regions composed of a metal layer formed to cause a surface plasmon resonance phenomenon and a dielectric constant regulation layer laminated on the metal layer may be provided for one optical path. In this case, the dielectric constant of each of the dielectric constant regulation layers laminated in the two or more detection regions is regulated so that the two or more detection regions have different surface plasmon resonances, and the dielectric constant regulation layer laminated in at last one of the two or more detection regions may be configured to function as a sensitive layer having sensitivity to an object to be detected.

In such a structure where two or more detection regions each have a dielectric constant regulation layer laminated therein, the dielectric constant regulation layers of the two or more detection regions may be configured to function as sensitive layers having sensitivity to different objects to be detected.

Here, the dielectric constant regulation layer is provided to achieve desired SPR conditions, and main factors for achieving desired SPR conditions are the complex dielectric constant of a material constituting the dielectric constant regulation layer and the thickness of the dielectric constant regulation layer. The complex dielectric constant of the dielectric constant regulation layer can be set to a desired value by changing the type of matrix itself, or by dispersing, in a matrix, particles including nanoparticles having a complex dielectric constant different from that of the matrix, or by making a matrix porous, that is, by dispersing small voids (in a broad sense, particles having a dielectric constant, such as air or liquid) in a matrix. The thickness of the dielectric constant regulation layer for achieving desired SPR conditions will be described later.

The "having sensitivity to an object to be detected" means that the dielectric constant regulation layer itself or its uppermost surface has sensitivity to an object to be detected so that when the object to be detected comes close to the dielectric constant regulation layer, SPR conditions are changed by, for example, adsorption to the surface of the dielectric constant regulation layer, absorption by the surface layer of the dielectric constant regulation layer, absorption by the sensitive layer, the occurrence of chemical reaction on the surface of the dielectric constant regulation layer, or binding to the surface of the dielectric constant regulation layer due to chemical reaction. For example, in a case where reflected light is measured as, for example, a wavelength spectrum, the wavelength of a resonance peak shifts. It is preferred that the dielectric constant regulation layer itself that functions as a sensitive layer or its surface has the ability to absorb an object to be detected or the surface of the dielectric constant regulation layer has the ability to adsorb or bind to an object to be detected. The phrase "the surface of the dielectric constant regulation layer has the ability to adsorb an object to be detected" means that, for example, the surface of the dielectric constant regulation layer can simply physically adsorb an object to be detected based on their hydrophilicity or hydrophobicity, or can electrostatically adsorb an object to be detected, or can adsorb an object to be detected by ionic bonding. On the other hand, the phrase "the surface of the dielectric constant regulation layer has the ability to bind to an object to be detected" means that the surface of the dielectric constant regulation layer has polar groups or functional groups so as to be able to bind to an object to be detected by chemical binding, antigen-antibody reaction, or another type of binding.

In a case where two or more dielectric constant regulation layers are provided in one detection region, at least the outermost dielectric constant regulation layer preferably functions as a sensitive layer.

The dielectric constant regulation layer does not always need to be transparent, but is preferably a transparent medium layer from the viewpoint of achieving a sharp surface plasmon resonance. When reflected light is measured as, for example, a wavelength spectrum, the use of a transparent medium layer makes it possible to narrow the half-width of a resonance absorption band. By narrowing the half-width of an absorption band, optical absorption bands that appear due to excitation of surface plasmon at the detection regions can be separated from each other for ease of measurement and multiplexing can be easily achieved. Examples of a material usable as the dielectric constant regulation layer include glass films, alkali-free glass films, silicon oxide films, quartz glass films, magnesium fluoride films, alumina films, titania films, silicon nitride films, ITO films, polyvinyl alcohol, polyacrylic acid, polystyrenesulfonic acid, polyallylamine, polydiallyldimethylammonium chloride, polyamide acid, polyimide precursors, polyvinylcarbazole, polymethylmethacrylate, waxes, polyimides, and Teflon (trademark).

In order to impart sensitivity to, for example, a hydrophilic or hydrophobic material to the dielectric constant regulation layer, a solvent-soluble material can be used as a material having sensitivity to be contained in a sensitive layer. More specifically, a material soluble in a hydrophilic solvent can be used for forming a layer having sensitivity to a hydrophilic material, and a material soluble in a hydrophobic solvent can be used for forming a layer having sensitivity to a hydrophobic material. Specific examples of a material soluble in a hydrophilic solvent include PVA (polyvinyl alcohol), polyamide acid, and polyimide precursors. Specific examples of a material soluble in a hydrophobic solvent include PVK (polyvinylcarbazole), PMMA (polymethylmethacrylate), waxes, polyimides, and Teflon (trademark). It is to be noted that from the viewpoint of enhancing hydrophobicity and improving durability, among polyimides, fluorinated polyimides are particularly preferably used as hydrophobic solvent-soluble materials.

Further, in order to impart sensitivity to ammonia or nitrogen dioxide, polyacrylic acid or polyallylamine can be used, respectively.

A method for forming the above-described dielectric constant regulation layer is not particularly limited, and any well-known film formation method such as spin coating, dip coating, or vacuum deposition can be used. Among these methods, spin coating or vacuum deposition is preferably used from the viewpoint of improving film thickness uniformity and reducing roughness. The improvement in film thickness uniformity makes it possible to reduce the half-width of a resonance absorption band, which reduces crosstalk between adjacent peaks and therefore multiplexing can be easily achieved. The reduction in roughness makes it possible to prevent scattering of detection light, which contributes to improvement in detection accuracy.

On the other hand, a layer that functions as a sensitive layer is preferably a layer made of a polymer containing a material having sensitivity, more preferably a layer made of a polymer in which a material having sensitivity is evenly dispersed. Examples of such a polymer include PVA (polyvinyl alcohol), polyamide acid, PVK (polyvinylcarbazole), PMMA (polymethylmethacrylate), waxes, polyimides, fluorinated polyimides, and polytetrafluoroethylene.

The thickness of the dielectric constant regulation layer can be set to a value in the range of 1 to 1500 nm, but as described above, it is not necessarily appropriate to suggest that the thickness of the dielectric constant regulation layer is in the range of 1 to 1500 nm because there is a case where the thickness of the dielectric constant regulation layer is controlled to allow the two or more detection regions to have different absorption peak wavelengths. For example, the thickness of the dielectric constant regulation layer can be set to a value in the range of 1 to 2000 nm when, for example, (1) the dielectric constant regulation layer has a low dielectric constant; (2) measurement is performed in the infrared region; or (3) measurement is performed by waveguide modes.

The absorption peak wavelengths of the two or more detection regions may be made different by allowing the dielectric constant regulation layers to have different thicknesses. When the dielectric constant regulation layers have the same dielectric constant, the difference in thickness between the dielectric constant regulation layers can be set to about 5 to 2000 nm, preferably about 10 to 1500 nm, more preferably about 20 to 500 nm, even more preferably about 30 to 200 nm, particularly preferably about 40 to 100 nm.

Even when the dielectric constant regulation layers have the same thickness, the absorption peak wavelengths of the two or more detection regions can be made different by allowing the dielectric constant regulation layers to have different dielectric constants. In a case where a layer having sensitivity (or insensitivity) to an object to be detected is not a layer formed by surface treatment or a molecular film but a layer provided on the surface of the dielectric constant regulation layer so as to have a substantial thickness, the dielectric constants of the dielectric constant regulation layers are preferably regulated (designed) to achieve desired SPR conditions comprehensively in consideration of the influence of the dielectric constant of the sensitive layer or the insensitive layer.

When a hydrophilic material is used as a material of the dielectric constant regulation layer of one of the two or more detection regions and a hydrophobic material is used as a material of the dielectric constant regulation layer of another of the two or more detection regions, a hydrophilic gas and a hydrophobic gas can be easily detected. That is, a hydrophilic gas and a hydrophobic gas selectively come into contact with (adsorb to) a sensitive layer using a hydrophilic material and a sensitive layer using a hydrophobic material, respectively, and therefore can be detected separately from each other.

When polyacrylic acid is used as a material of a sensitive layer of one of the two or more detection regions and polyallylamine is used as a material of a sensitive layer of another of the two or more detection regions, the former has sensitivity to ammonia and the latter has sensitivity to nitrogen dioxide, and therefore ammonia and nitrogen dioxide can be detected separately from each other.

Further, the interference of humidity in detection of, for example, nitrogen dioxide can also be detected by using such two or more sensitive layers. More specifically, when two sensitive layers are used, one of the two sensitive layers is made sensitive to humidity by using a water-soluble polymer and the other sensitive layer is made sensitive to humidity and nitrogen dioxide by using a pH indicator for nitrogen dioxide detection. In this case, the amount of adsorbed nitrogen dioxide can be accurately determined by subtracting the contribution of humidity monitored by the former from the result measured by the latter.

Further, a detection region composed of a metal layer may be provided without providing any sensitive layer thereon. In a case where a detection region composed of a metal layer is used, surface plasmon can be excited by, for example, using the sensor in a liquid such as water so that a dielectric constant is regulated by the liquid. In this case, reference light can be obtained by providing an optical path having no detection region. Alternatively, results measured in an environment which has a different dielectric constant and in which surface plasmon excitation does not occur, such as in air, can be used as reference.

In the present invention, a dielectric constant regulation layer laminated in at least one of the two or more detection regions, which is different from the detection region in which a dielectric constant regulation layer that functions as a sensitive layer having sensitivity to an object to be detected is laminated, may function as an insensitive layer not having sensitivity to an object to be detected.

Here, the "dielectric constant regulation layer functions as an insensitive layer not having sensitivity to an object to be detected" means that the dielectric constant regulation layer itself or the surface thereof has insensitivity to an object to be detected, and therefore even when an object to be detected comes close to the dielectric constant regulation layer, SPR conditions of the dielectric constant regulation layer do not vary due to, for example, adsorption to the surface of the dielectric constant regulation layer, absorption by the surface layer of the dielectric constant regulation layer, absorption by the dielectric constant regulation layer, the occurrence of chemical reaction on the surface of the dielectric constant regulation layer, or binding to the surface of the dielectric constant regulation layer by chemical reaction. For example, a material that does not cause selective adsorption (in some fields, often referred to as "specific adsorption") to an object to be detected can be used for forming an insensitive layer because SPR conditions do not vary. In a case where reflected light is measured as, for example, a wavelength spectrum, the wavelength shift of a resonant peak does not occur.

The wavelength shift may be detected by spectral observation or may be detected as a change in intensity by monitoring the intensity of output light at a certain wavelength position close to the resonant peak. Alternatively, the wavelength shift may be detected by monitoring the intensity of light separated by a filter having certain wavelength characteristics in the vicinity of the resonant peak.

In this case, the dielectric constant regulation layer that functions as an insensitive layer is preferably made of one material selected from the group consisting of glass films, alkali-free glass films, silicon oxide films, quartz glass films, magnesium fluoride films, alumina films, titania films, silicon nitride films, and ITO (indium tin oxide) films. It is to be noted that the composition of the material of each of these films constituting the insensitive layer does not always correspond with a composition formula representing the material. This is because a film formed by, for example, vapor deposition does not always have composition corresponding with a composition formula representing the material of the film.

The dielectric constant regulation layer that functions as an insensitive layer may be composed of a single layer or two or more layers as long as at least its surface has insensitivity to an object to be detected. For example, the dielectric constant regulation layer that functions as an insensitive layer may have one or more sensitive layers as long as an insensitive layer is provided as an uppermost layer.

The thickness of the insensitive layer can be set to a value in the range of 1 to 2000 nm, but is preferably set to a value in the range of 10 to 1500 nm.

The insensitive layer can be formed in the same manner as described above with reference to the dielectric constant regulation layer.

As described above, in the SPR sensor according to the present invention, the detection regions are provided at two or more positions on one optical path. The two or more detection regions may be provided on the same plane of one optical path, or may be provided on the two upper and lower side surfaces of one optical path, or may be provided on the two right and left side surfaces of one optical path.

The two or more detection regions may be provided on the upper and right side surfaces of one optical path. In this case, detection (demultiplexing) can be performed using polarization components. This is based on that surface plasmon is excited by a p-polarization component. The positions of the detection regions provided on the upper and right side surfaces of one optical path can be selected by detecting components that act as p-polarized waves at the upper detection region and the right detection region, respectively. When waveguide modes are used, waveguide modes can be excited by both p- and s-polarized waves, but excitation conditions are generally different and therefore detection signals can be detected using p- and s-polarization components.

Further, the detection regions may be provided on the four upper, lower, right, and left side surfaces of one optical path. In this case, however, the positions of the detection regions need to be set in consideration of the plane of polarization in the same manner as described above.

For example, in the case of a structure in which surface plasmon can be excited by a p-polarization component at detection regions, detection signals are detected using a p-polarization component and an s-polarization component is used as reference light. In this case, detection sensitivity and detection accuracy can be improved by measuring a difference spectrum. That is, in a case where an optical path for detection and an optical path for reference light are provided separately from each other, there is a possibility that optical errors are caused by minute differences in structure between these optical paths, but such a possibility can be eliminated by using a common optical path, thereby improving detection accuracy. Therefore, detection using an optical path where two or more detection regions are provided is preferably performed using a p-polarization component as detection light and an s-polarization component as reference light. Further, such a structure is advantageous from the viewpoint of detection operation because, for example, the operation of changing the position of a light source between when detection light is used and when reference light is used can be omitted.

As described above, the SPR sensor according to the present invention allows multichannel detection to be performed by one optical path. However, such a structure allows not only multichannel detection but also detection of reference light to be performed by one optical path, and is therefore particularly useful for the present invention aiming to achieve miniaturization and cost reduction.

In a case where detection regions are formed close to each other, detection windows may be provided to improve the accuracy of, for example, the area of each of the detection regions. Such detection windows can be provided by, for example, photolithography using the same masks so that two or more detection regions are exposed through openings having the same area (or through openings having predetermined different areas) by covering a region other than the detection regions with an insensitive material. This makes it possible to improve quantitativity and reproducibility of detected data obtained by two or more detection regions. In order to provide detection windows, a boundary region where the thickness of a dielectric constant regulation layer is changed between adjacent detection regions or a boundary region where the material of a dielectric constant regulation layer is changed between adjacent detection regions is made insensitive by, for example, covering such a boundary region with an insensitive material. This makes it possible to avoid the influence of cross-contamination of data from adjacent detection regions, thereby improving quantitativity, reproducibility, and S/N ratio of detected data.

Further, detection light having a single wavelength can also be used. More specifically, a single wavelength laser light source can be used. For example, in the case of a structure in which different detection regions are provided on upper and right side surfaces of one optical path, detection light is allowed to enter the structure while polarization components in both vertical and horizontal directions are scrambled by a polarization scrambler, and a polarized wave having an electric field component in the vertical direction (which acts as a p-polarized wave at the upper side surface but acts as an s-polarized wave at the right side surface) and a polarized wave having an electric field component in the horizontal direction (which acts as an s-polarized wave at the upper side surface but acts as a p-polarized wave at the right side surface) are separated from each other by a PBS (polarization beam splitter). This makes it possible to distinguish a detection signal detected by the detection region provided on the upper side surface and a detection signal detected by the detection region provided on the right side surface from each other.

Further, in the case of the same structure as described above where incident light is a linearly-polarized wave propagating in a certain direction and detection light includes all the polarization components, a detection signal can be selectively obtained by the detection region provided on the upper side surface when the incident light is polarized in the vertical direction, and a detection signal can be selectively obtained by the detection region provided on the right side surface when the incident light is polarized in the horizontal direction. Further, when incident light is allowed to enter the structure while the plane of polarization is rotated, detection light is allowed to enter the optical path in a time-division manner, and therefore a detection signal detected by the detection region provided on the upper side surface and a detection signal detected by the detection region provided on the right side surface can be alternately obtained.

As incident light for detection, white light can be used. In this case, a spectrometer needs to be provided on the detector side. That is, the resonant wave number can be obtained by monitoring the spectral intensity of output light (reflected light).

Alternatively, a light source that emits light of two or more wavelengths corresponding to the detection wavelengths of the two or more detection regions may be used. In this case, a wavelength multiplexing device such as a multiplexing/branching unit is used to allow incident light to enter the optical path and to separate output light into signals. Further, this form is suitable for remote detection using an optical fiber because a sensor unit does not need power supply and incident light and output light are allowed to remotely enter and exit the sensor unit using an optical fiber. On the other hand, a compact device can be achieved by integrating an optical path unit (optical waveguide) with a multiplexing/branching unit.

Different polarized waves having the same wavelength may be allowed to simultaneously enter the optical path. In this case, the sensor needs to be used together with an unpolarized light source or a polarization scrambler.

In a case where monochromatic light (having a single wavelength) is used as detection light, the monochromatic light is allowed to enter the optical path through a prism by a prism-coupler method and output light is allowed to exit the optical path through a prism. However, in a case where white light is used as detection light, it is difficult to allow incident light and output light to enter and exit the optical path by a prism-coupler method because incidence conditions vary with the wavelength. Therefore, in this case, a method in which incident light is allowed to enter the optical path through its end face and output light is allowed to exit the optical path through its other end face is suitable. Further, in a case where white light is used as detection light, a well-known method, in which the end of an optical fiber is arranged in a liquid drop placed on an optical waveguide to simultaneously satisfy many incidence conditions, may be used together with the above method.

When one and the same specimen (object to be detected) is guided to the two or more detection regions of the SPR sensor according to the present invention, concentration difference•concentration gradient can be detected by utilizing the difference in position between the detection regions.

Even when one and the same specimen (object to be detected) is guided to the two or more detection regions, one or more other detection regions suitable for a specimen different from the specimen guided to the two or more detection regions may be provided to allow the different specimen to be detected. Such a structure makes it possible to simultaneously detect two or more properties of a certain specimen or to detect components of a mixture specimen.

Further, the SPR sensor according to the present invention may be configured to allow different specimens to be guided to different detection regions. This structure makes it possible to perform simultaneous detection of many specimens, detection of two-dimensionally spotted DNA specimens, and detection of antigen-antibody reaction. In a case where the SPR sensor according to the present invention is two-dimensionally used, one zigzag optical path is provided or two or more detection regions are arranged in an array.

Although not shown in the drawings, two or more optical paths each having two or more detection regions may be arranged in parallel to further increase the number of detection regions. This makes it possible to obtain an SPR sensor capable of simultaneously detecting many objects to be detected.

Hereinafter, 6 variations of the SPR sensor according to the present invention will be described.

Figure 3:
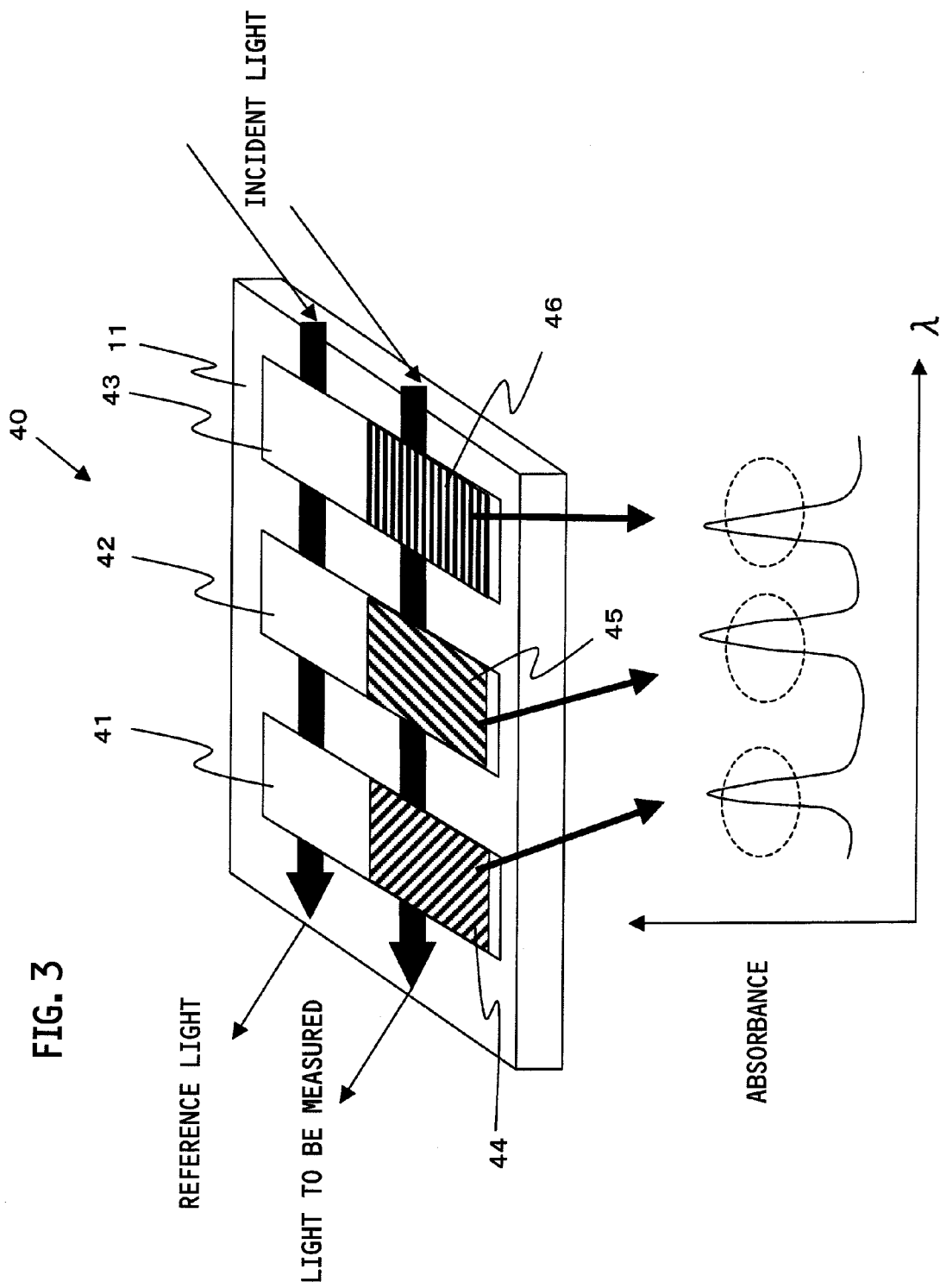
FIG. 3 is a schematic perspective view of another example of the SPR sensor according to the present invention in which three detection regions are provided.

FIG. 3 shows an example of an SPR sensor capable of performing three-channel simultaneous detection using three detection regions. An SPR sensor 40 shown in FIG. 3 includes three detection regions provided on the transparent substrate 11. The three detection regions have metals layers 41, 42, and 43, respectively, and dielectric constant regulation layers 44, 45, and 46 are provided on the metal layers 41, 42, and 43, respectively. The dielectric constant of each of the dielectric constant regulation layers 44, 45, and 46 is regulated so that the three detection regions have different surface plasmon resonances. The outermost layer of each of the detection regions is configured as a sensitive layer, and the three sensitive layers are made of different materials. Further, the dielectric constant regulation layers 44 and 46 are different in thickness from the dielectric constant regulation layer 45. As shown below the SPR sensor 40 in FIG. 3, this structure allows the three detection regions to have different absorption peak wavelengths, and therefore objects to be detected present on the three detection regions can be simultaneously detected. In this case, all the dielectric constant regulation layers are configured to function as sensitive layers, but at least one of the dielectric constant regulation layers may be configured to function as an insensitive layer.

It is to be noted that the metal layers 41, 42, and 43 may be made of different metals.

The SPR sensor 40 shown in FIG. 3 is configured to have three detection regions, but may be configured to have four or more detection regions in the same manner as described above.

Figure 4:
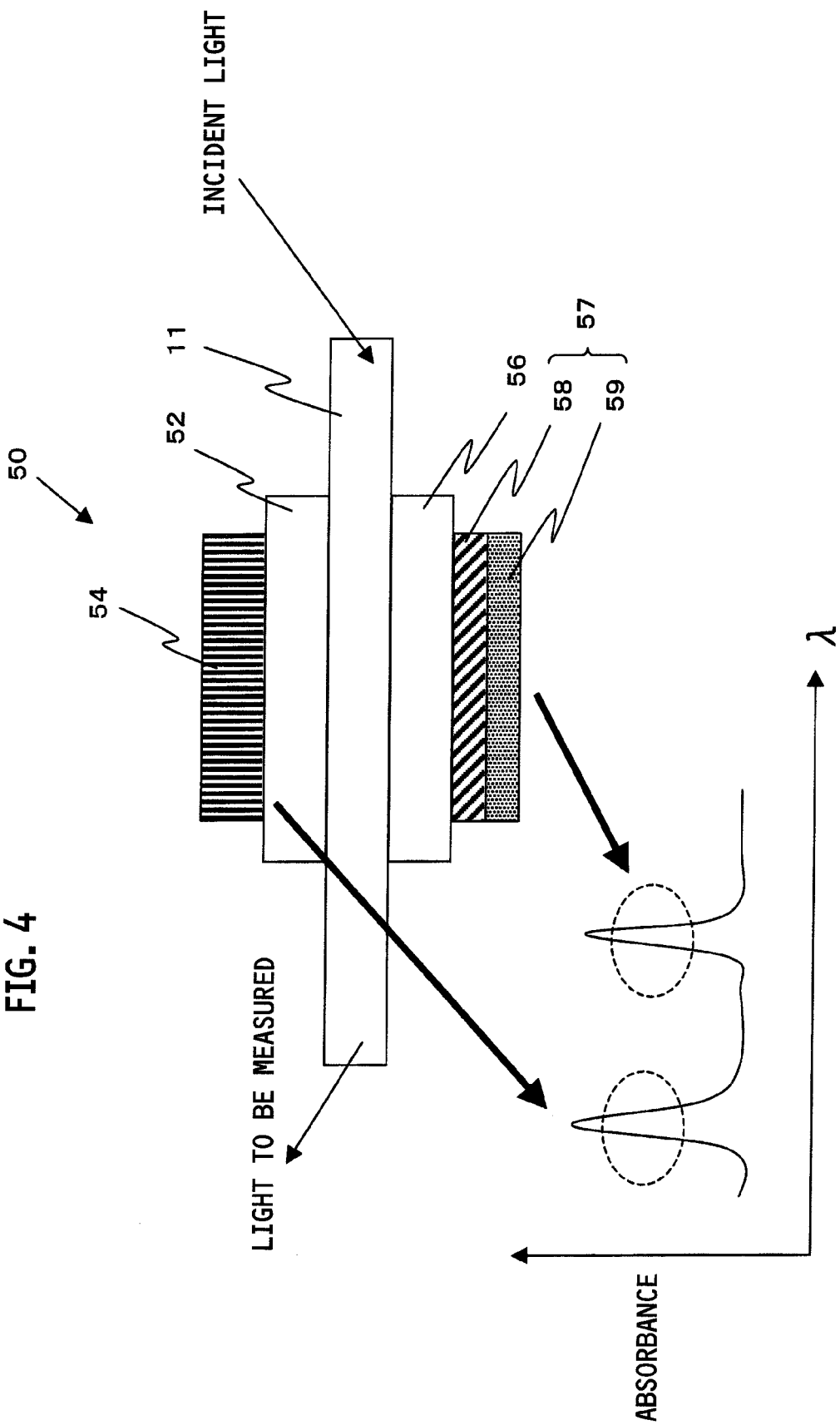
FIG. 4 is a schematic side view of another example of the SPR sensor according to the present invention in which detection regions are provided on both side surfaces of a transparent substrate.

FIG. 4 shows an example of an SPR sensor having detection regions on both surfaces of a transparent substrate. An SPR sensor 50 shown in FIG. 4 has two detection regions on both surfaces of the transparent substrate 11. One of the two detection regions is formed by laminating, on one of the two surfaces of the transparent substrate 11, a metal layer 52 and a dielectric constant regulation layer 54 serving as a sensitive layer in this order. The other detection region is formed by laminating, on the other surface of the transparent substrate 11, a metal layer 56 and a dielectric constant regulation layer 57 in this order. The dielectric constant regulation layer 57 is composed of two layers, that is, an insensitive layer 58 provided on the metal layer 56 and a sensitive layer 59 provided on the insensitive layer 58. The dielectric constant of each of the dielectric constant regulation layers of the detection regions provided on both surfaces of the transparent substrate is regulated so that the two detection regions have different surface plasmon resonances. The two dielectric constant regulation layers function as sensitive layers made of different materials. As shown below the SPR sensor 50 in FIG. 4, this structure also allows the two detection regions to have different absorption peak wavelengths, and therefore objects to be detected present on the two detection regions can be simultaneously detected.

The structure shown in FIG. 4 can be further reduced in depth as compared to the structure in which two detection regions are provided on an optical path along the direction of light propagation (see FIG. 1).

Figure 5:
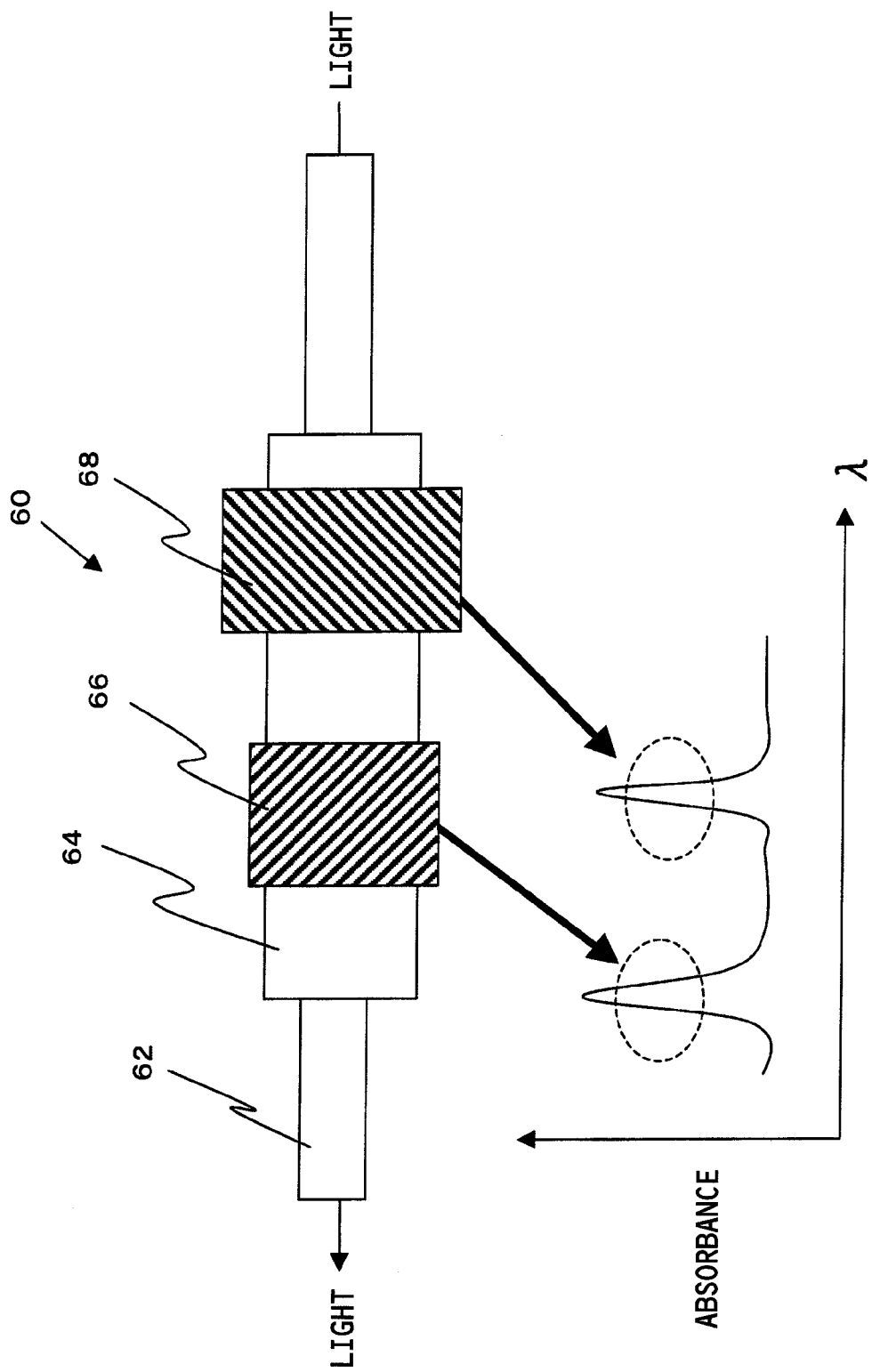
FIG. 5 is a schematic side view of another example of the SPR sensor according to the present invention in which detection regions are provided on an optical fiber.

FIG. 5 shows an example of an SPR sensor formed by providing two detection regions on a linear optical fiber instead of a planar substrate such as a transparent substrate. An SPR sensor 60 shown in FIG. 5 has an optical fiber 62 and a metal layer 64 provided on the surface of the optical fiber 62. On part of the surface of the metal layer 64, two regions are provided as detection regions. One of the detection regions is provided by forming a dielectric constant regulation layer 66 as a sensitive layer, and the other detection region is provided by forming a dielectric constant regulation layer 68. The dielectric constant of each of the dielectric constant regulation layers of the two detection regions is regulated so that the two detection regions have different surface plasmon resonances. The two dielectric constant regulation layers function as sensitive layers made of different materials. As shown below the SPR sensor 60 in FIG. 5, this structure also allows the two detection regions to have different absorption peak wavelengths, and therefore objects to be detected present on the two detection regions can be simultaneously detected.

Figure 6:
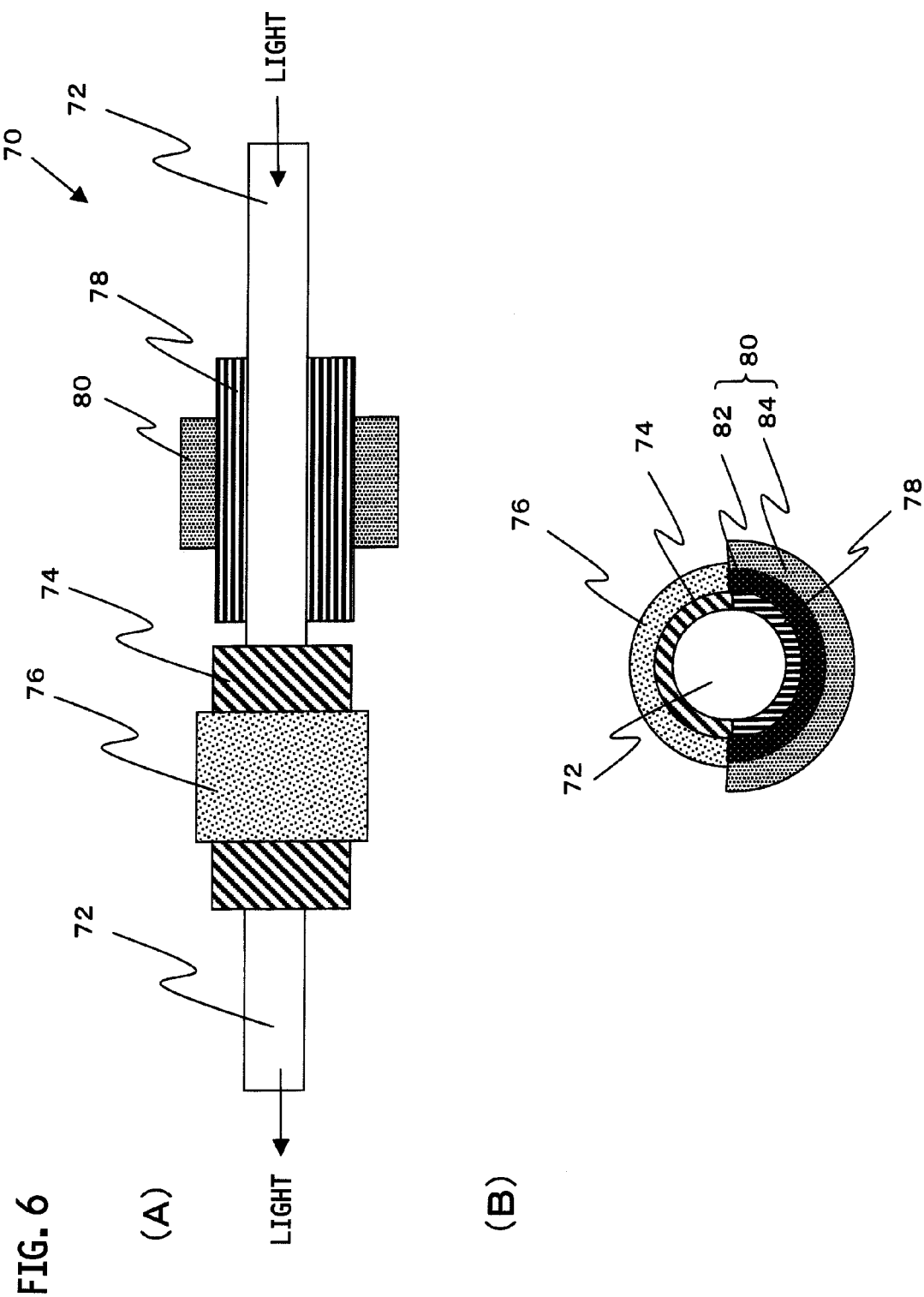
FIG. 6 is a schematic side view of another example of the SPR sensor according to the present invention in which detection regions are provided on an optical fiber at different positions along the circumferential direction of the optical fiber.

An SPR sensor shown in FIG. 6 also uses an optical fiber as in the case of the SPR sensor shown in FIG. 5. As shown in FIG. 6, an SPR sensor 70 has two detection regions on an optical fiber. FIG. 6(A) is a schematic view of the SPR sensor 70 when viewed from the direction of its side surface, and FIG. 6(B) is a schematic view of the SPR sensor 70 when viewed from the direction of the end face of the optical fiber. The SPR sensor 70 shown in FIG. 6 has a metal layer 74 provided on part of the surface of the optical fiber 72 so as to cover one-half of the circumference of the optical fiber 72 along the circumferential direction. Further, a dielectric constant regulation layer 76 is provided as a sensitive layer on the metal layer 74. The SPR sensor 70 also has a metal layer 78 provided in a region different from the region where the metal layer 74 is provided. The metal layer 78 is provided in a semi-circular region located in a symmetrical position with respect to the semi-circular region where the metal layer 74 is provided. Further, a dielectric constant regulation layer 80 is provided on the metal layer 78. The dielectric constant regulation layer 80 is composed of two layers, that is, an insensitive layer 82 provided on the metal layer 78 side and a sensitive layer 84 provided on the insensitive layer 82. The dielectric constant of each of the dielectric constant regulation layers of the two detection regions is regulated so that the two detection regions have different surface plasmon resonances. The two dielectric constant regulation layers function as sensitive layers made of different materials. This structure also allows the two detection regions to have different absorption peak wavelengths, and therefore objects to be detected present on the two detection regions can be simultaneously detected.

Figure 7:
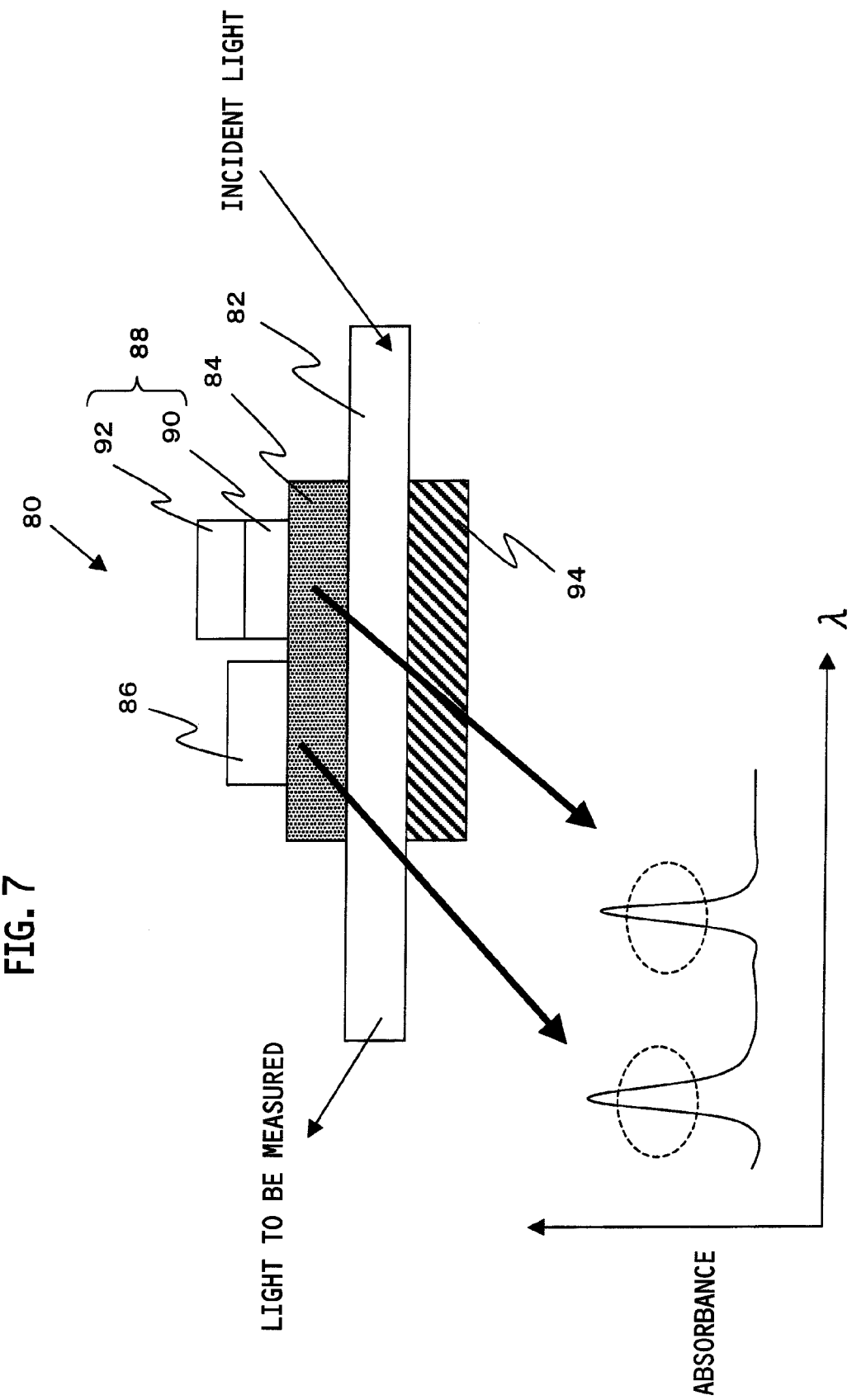
FIG. 7 is a schematic side view of another example of the SPR sensor according to the present invention which is combined with a QCM.

On the other hand, the SPR sensor according to the present invention may be combined with a QCM (Quartz Crystal Microbalance) sensor. FIG. 7 is a schematic view showing the structure of the SPR sensor according to the present invention combined with a QCM sensor. An SPR sensor 80 shown in FIG. 7 has a metal layer 84 provided on one of the surfaces of a QCM quartz substrate 82 as a transparent substrate and dielectric constant regulation layers 86 and 88 provided at two positions on the metal layer 84. The dielectric constant regulation layer 86 is configured to function as a sensitive layer. The dielectric constant regulation layer 88 is composed of an insensitive layer 90 located on the QCM quartz substrate 82 side and a sensitive layer 92. The dielectric constant of each of the dielectric constant regulation layers of the two detection regions is regulated so that the two detection regions have different surface plasmon resonances. The dielectric constant regulation layers are configured to function as sensitive layers made of different materials. This structure is the same as the structure of the SPR sensor having two detection regions described above with reference to FIG. 1.

As described above, the metal layer 84 is used to excite a surface plasmon wave, but also serves as a QCM electrode in this structure. Further, a QCM electrode 94 is provided on the other surface of the QCM quartz substrate 82. That is, the QCM quartz substrate 82 is sandwiched between the two electrodes 84 and 94, and therefore the QCM quartz substrate 82 and the electrodes 84 and 94 constitute a QCM sensor. The QCM electrode 94 is in contact with the QCM quartz substrate as a transparent substrate and also serves as an optical path, and is therefore preferably formed to be thick (200 nm or more) to provide a mirror surface.

The SPR sensor 80 having the structure described above functions as both an SPR sensor and a QCM sensor.

Figure 8:
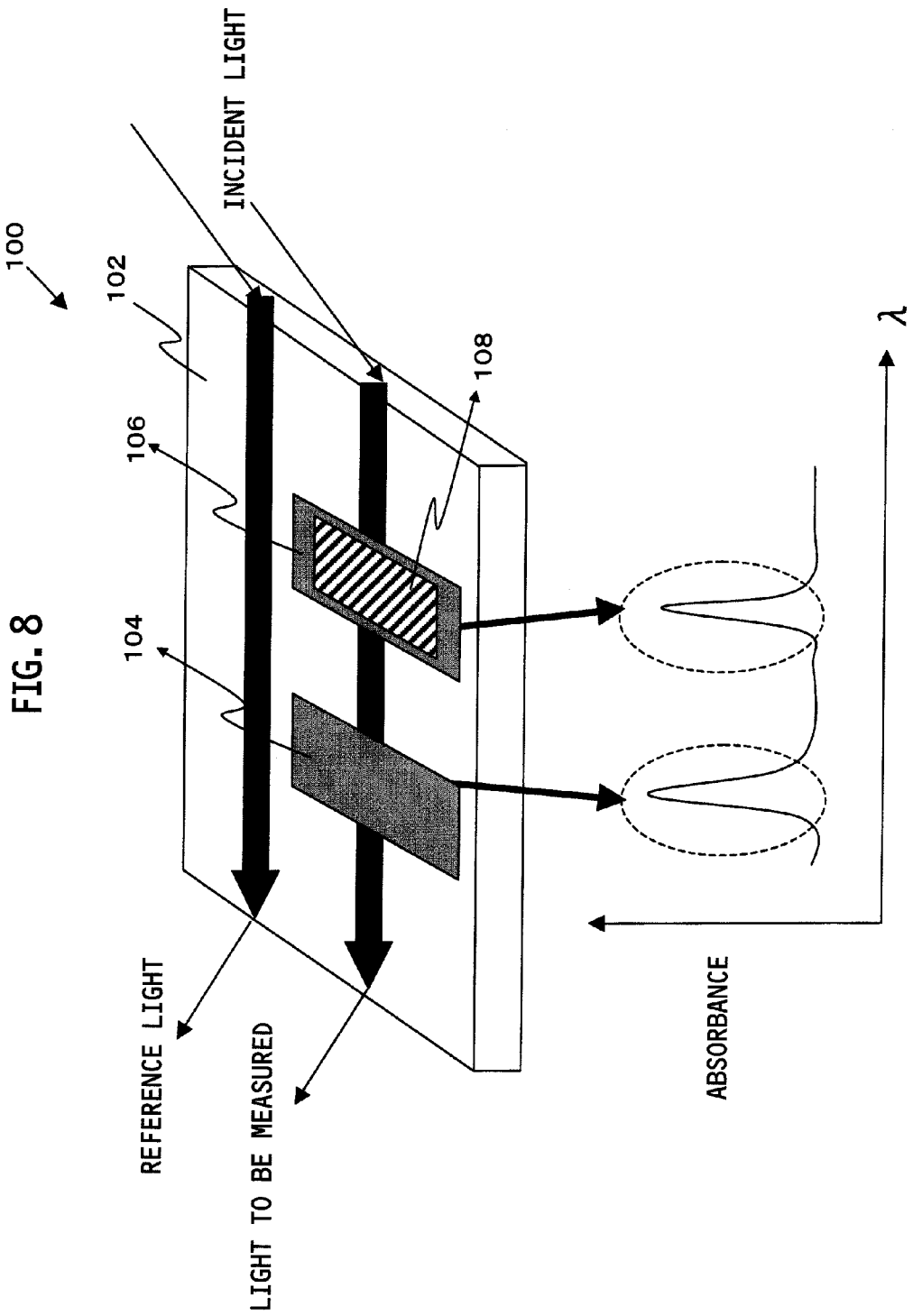
FIG. 8 is a schematic perspective view of another example of the SPR sensor according to the present invention in which a detection region composed of a metal layer and a detection region composed of a metal layer and a dielectric constant regulation layer are provided.

FIG. 8 shows an example of an SPR sensor capable of achieving two-channel simultaneous detection using a detection region composed of a metal thin film and a detection region composed of a metal thin film and a dielectric constant regulation layer. An SPR sensor 100 shown in FIG. 8 includes a transparent substrate 102 and two detection regions provided on the transparent substrate 102. One of the detection regions is composed of only a metal layer 104, and the other detection region is composed of a metal layer 106 and a dielectric constant regulation layer 108 laminated on the metal layer 106. The dielectric constant of the dielectric constant regulation layer 108 is regulated so that the metal layer 104 and the metal layer 106 have different surface plasmon resonances in a liquid (e.g., in water) in which measurement is performed. The dielectric constant regulation layer 108 functions as a sensitive layer. As shown below the SPR sensor 100 in FIG. 8, this structure allows the detection regions of the SPR sensor 100 to have different absorption peak wavelengths when the SPR sensor 100 is immersed in a liquid during measurement, and therefore objects to be detected present on the two detection regions can be simultaneously detected. In this case, reference light can be measured by using part of the transparent substrate 102 not including the detection regions as an optical path. Alternatively, light measured by placing the sensor 100 in a liquid having a dielectric constant significantly different from that of a liquid in which measurement is performed or in air so that surface plasmon cannot be excited may be used as reference light.

It is to be noted that the metal layers 104 and 106 may be made of different metals.

The SPR sensor shown in FIG. 8 has two detection regions, but may be configured to have three or more detection regions by using different dielectric constant regulation layers.

EXAMPLES

Hereinafter, the present invention will be described more specifically with reference to the following examples, but is not limited to these examples.

Example 1

First, a slide glass (26 mm×26 mm) was prepared as a transparent substrate. Then, a 50-nm-thick layer made of Ag was formed as a metal layer on the slide glass by vacuum vapor deposition. At this time, the metal layers (7 mm×18 mm) were formed in two regions for use as detection regions by using a mask so that no metal layer was formed in a region other than the two regions. Then, as shown in FIG. 1, a 10 mg/mL PVK solution (solvent: toluene) was applied onto one-half of the surface of one of the two metal layers by a casting method to form a 20-nm-thick dielectric constant regulation layer (sensitive layer). On the other hand, a 100-nm-thick $MgF_2$ layer was formed by vacuum vapor deposition on one-half of the surface of the other metal layer, and then a 20 mg/mL PVA solution (solvent: pure water) was applied onto the $MgF_2$ layer by a casting method to form a 10-nm-thick sensitive layer so that a dielectric constant regulation layer composed of the $MgF_2$ layer and the PVA layer was formed. In this way, an SPR sensor of Example 1 was produced.

Figure 9:
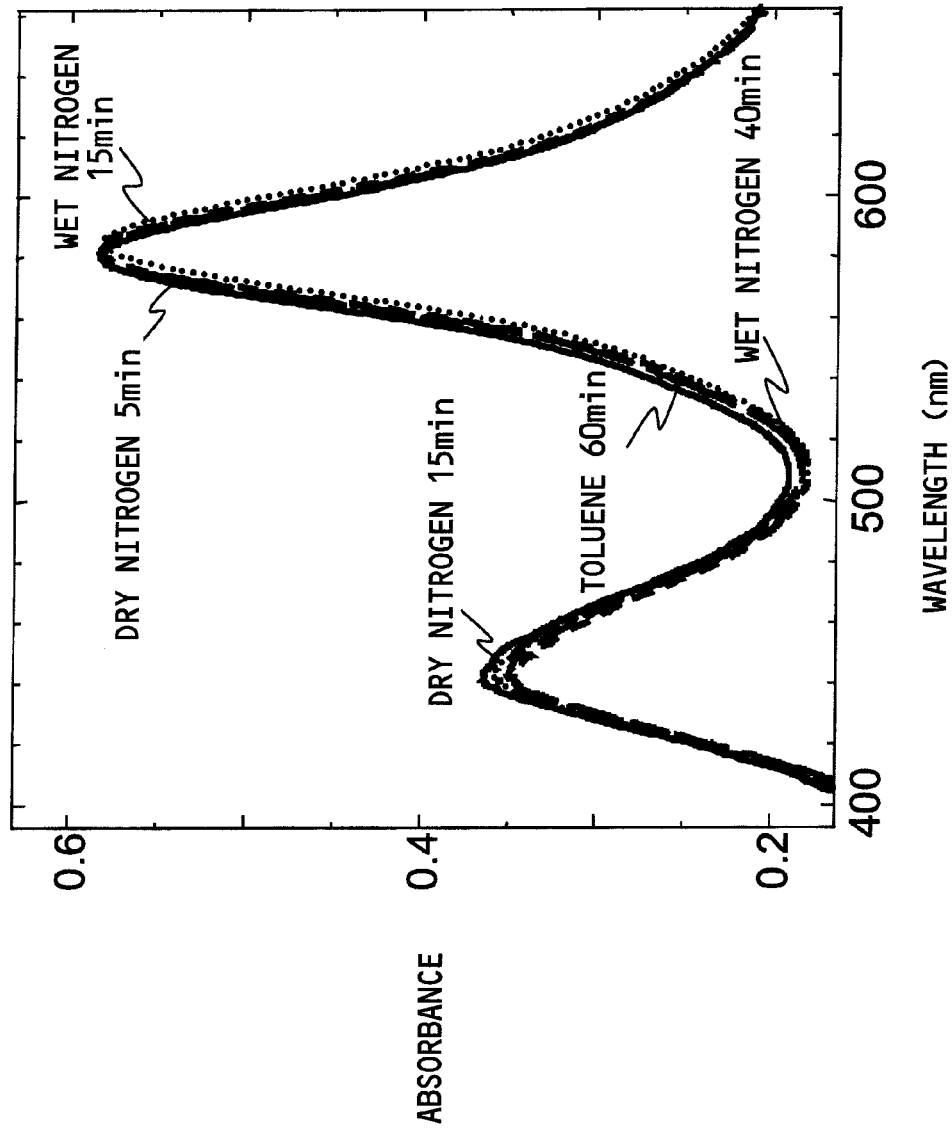
FIG. 9 shows absorption spectra measured by introducing different gases into a detection device using an SPR sensor produced in Example 1.

A detection device such as one shown in FIG. 2 was produced using the SPR sensor of Example 1. Then, dry nitrogen passed through silica gel, wet nitrogen obtained by bubbling nitrogen in pure water, and toluene-nitrogen obtained by bubbling nitrogen in toluene were introduced as gases to be detected into the detection device one after another. More specifically, dry nitrogen was introduced for 5 minutes, and then wet nitrogen was introduced for 15 minutes, and then dry nitrogen was introduced for 15 minutes, and then toluene-nitrogen was introduced for 60 minutes, and then dry nitrogen was introduced for 40 minutes. As a light source for detection, a xenon lamp (LHX-300 manufactured by Koken Kogyo K.K.) was used. As a detector, an instantaneous multichannel photodetector system (USB-2000 manufactured by Ocean Optics Inc.) was used. The thus obtained absorption spectra are shown in FIG. 9. Reference light was measured using an optical path having Ag thin films on which no dielectric constant regulation film was laminated, and detection light was measured using an optical path having Ag thin films on which the dielectric constant regulation layer was laminated (the same goes for Examples 2 and 3). FIG. 10(a) is an enlarged view of the absorption spectra shown in FIG. 9, which shows absorption peaks that appear on the short-wavelength side and FIG. 10(b) is an enlarged view of the absorption spectra shown in FIG. 9, which shows absorption peaks that appear on the long-wavelength side. In FIGS. 9 and 10, the absorption peaks on the long-wavelength side are due to surface plasmon excited at the region where the $MgF_2$ layer and the PVA layer are laminated on the metal layer and the absorption peaks on the short-wavelength side are due to surface plasmon excited at the region where the PVK layer is laminated on the metal layer. As can be seen from FIGS. 9 and 10, the absorption peaks on the short-wavelength side and the absorption peaks on the long-wavelength side show different responses. More specifically, the absorption peaks on the long-wavelength side strongly respond to humidity due to strong moisture absorbency of PVA, and therefore the peak wavelength is shifted to the long-wavelength side by introducing wet nitrogen and returned to near the initial level by introducing dry nitrogen. On the other hand, as can be seen from FIGS. 9 and 10, the absorption peaks on the short-wavelength side poorly respond to humidity due to low moisture absorbency of PVK.

Example 2

Metal layers were formed in two regions on a slide glass in the same manner as in Example 1. Then, a 20 mg/mL PVA solution (solvent: pure water) was applied onto one-half of the surface of one of the two metal layers by a casting method to form a 10-nm-thick dielectric constant regulation layer (sensitive layer). On the other hand, a 90-nm-thick $MgF_2$ layer was formed by vacuum vapor deposition on one-half of the surface of the other metal layer, and then a 6 mg/mL PMMA solution (solvent: acetone) was applied onto the $MgF_2$ layer by a casting method to form a 10-nm-thick PMMA layer (sensitive layer) so that a dielectric constant regulation layer composed of the $MgF_2$ layer and the PMMA layer was formed.

Figure 11:
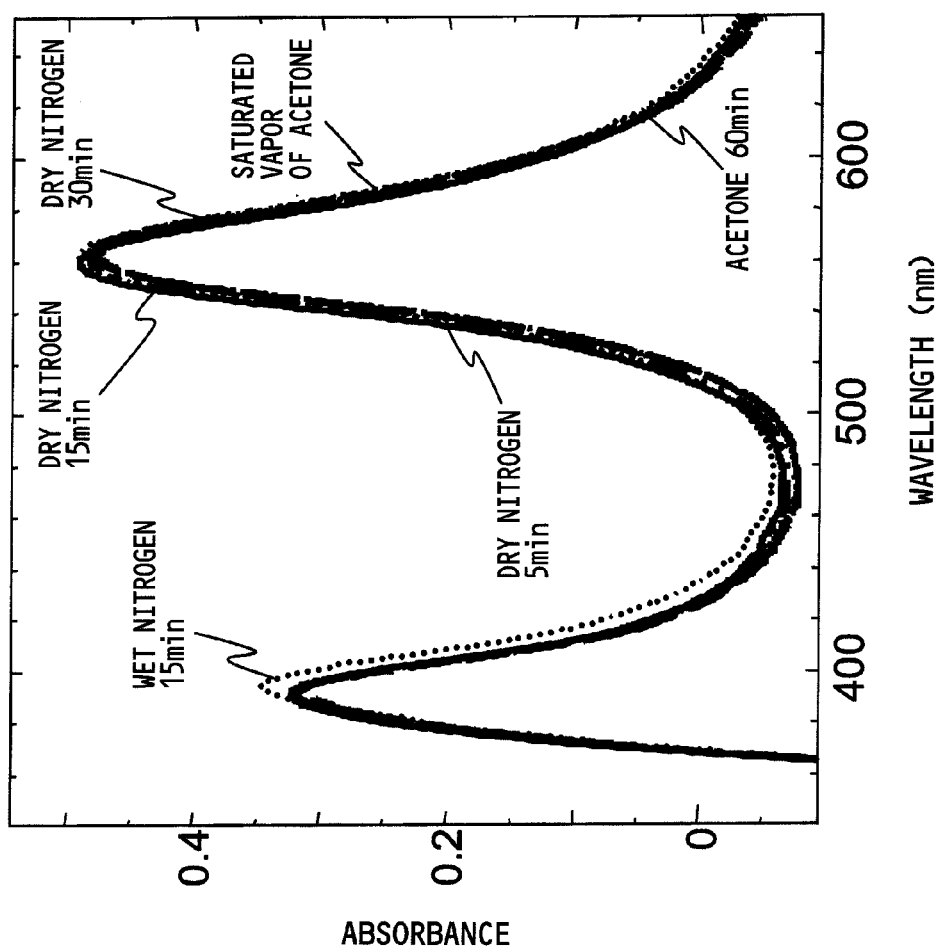
FIG. 11 shows absorption spectra measured by introducing different gases into a detection device using an SPR sensor produced in Example 2.
Figure 12:
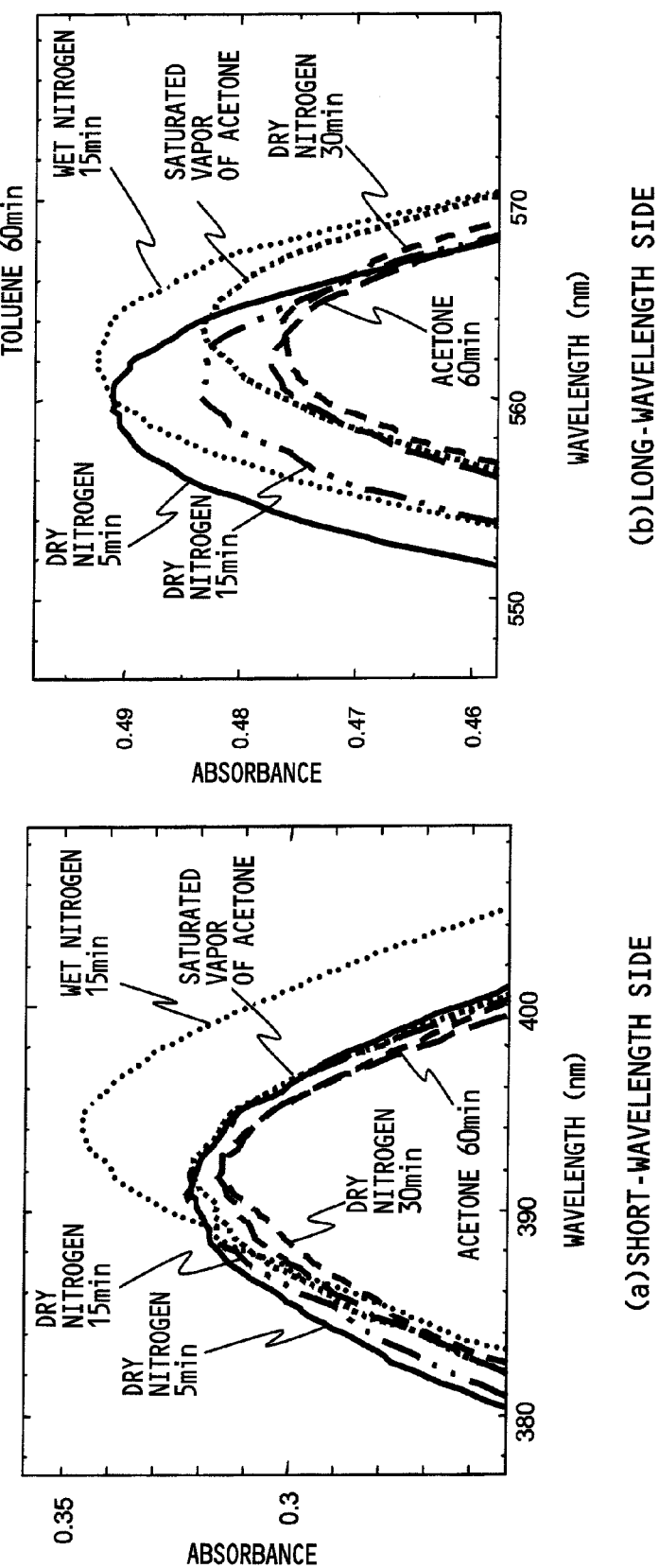
FIG. 12(a) is an enlarged view of the absorption spectra shown in FIG. 11, which shows absorption peaks on the short-wavelength side.
FIG. 12(b) is an enlarged view of the absorption spectra shown in FIG. 11, which shows absorption peaks on the long-wavelength side.

Then, a detection device such as one shown in FIG. 2 was produced in the same manner as in Example 1. Then, dry nitrogen passed through silica gel, wet nitrogen obtained by bubbling nitrogen in pure water, and acetone-nitrogen obtained by bubbling nitrogen in acetone were introduced as gases to be detected into the detection device one after another. More specifically, dry nitrogen was introduced for 5 minutes, and then wet nitrogen was introduced for 15 minutes, and then dry nitrogen was introduced for 15 minutes, and then toluene-nitrogen was introduced for 60 minutes. Further, saturated vapor of acetone was introduced for 10 minutes, and then dry nitrogen was introduced for 30 minutes. FIG. 11 shows absorption spectra obtained in the same manner as in Example 1. FIG. 12(a) is an enlarged view of the absorption spectra shown in FIG. 11, which shows absorption peaks that appear on the short-wavelength side and FIG. 12(b) is an enlarged view of the absorption spectra shown in FIG. 11, which shows absorption peaks that appear on the long-wavelength side. In FIGS. 11 and 12, the absorption peaks on the short-wavelength side are due to surface plasmon excited at the region where the PVA layer is laminated on the metal layer and the absorption peaks on the long-wavelength side are due to surface plasmon excited at the region where the $MgF_2$ layer and the PMMA layer are laminated on the metal layer. As can be seen from FIGS. 11 and 12, the absorption peaks on the short-wavelength side and the absorption peaks on the long-wavelength side show different responses. More specifically, the absorption peaks on the short-wavelength side strongly respond to humidity due to strong moisture absorbency of PVA, and therefore the peak wavelength is shifted to the long-wavelength side by introducing wet nitrogen and returned to the initial level by introducing dry nitrogen. Further, the absorption peaks on the short-wavelength side are poorly responsive to acetone. On the other hand, the absorption peaks on the long-wavelength side are less responsive to humidity than PVA due to weak moisture absorbency of PMMA. However, PMMA adsorbs acetone, and therefore the peak wavelength is shifted to the long-wavelength side by exposure to acetone vapor. As can be seen from the results, the use of different sensitive layers makes it possible to observe their different responses to various gases.

Example 3

Metal layers were formed in two regions on a slide glass in the same manner as in Example 1. Then, a mixture of a 5 mg/mL PVK solution and a 10 mg/mL octadecane solution (solvent: toluene) was applied onto one-half of the surface of one of the two metal layers by a dip coating method to form a 40-nm-thick dielectric constant regulation layer (sensitive layer). On the other hand, a 100-nm-thick $MgF_2$ layer was formed by vacuum vapor deposition on one-half of the surface of the other metal layer, and then a 10 mg/mL PVA solution (solvent: pure water) was applied onto the $MgF_2$ layer by a dip coating method to form a 55-nm-thick PVA layer (sensitive layer) so that a dielectric constant regulation layer composed of the $MgF_2$ layer and the PVA layer was formed.

Figure 13:
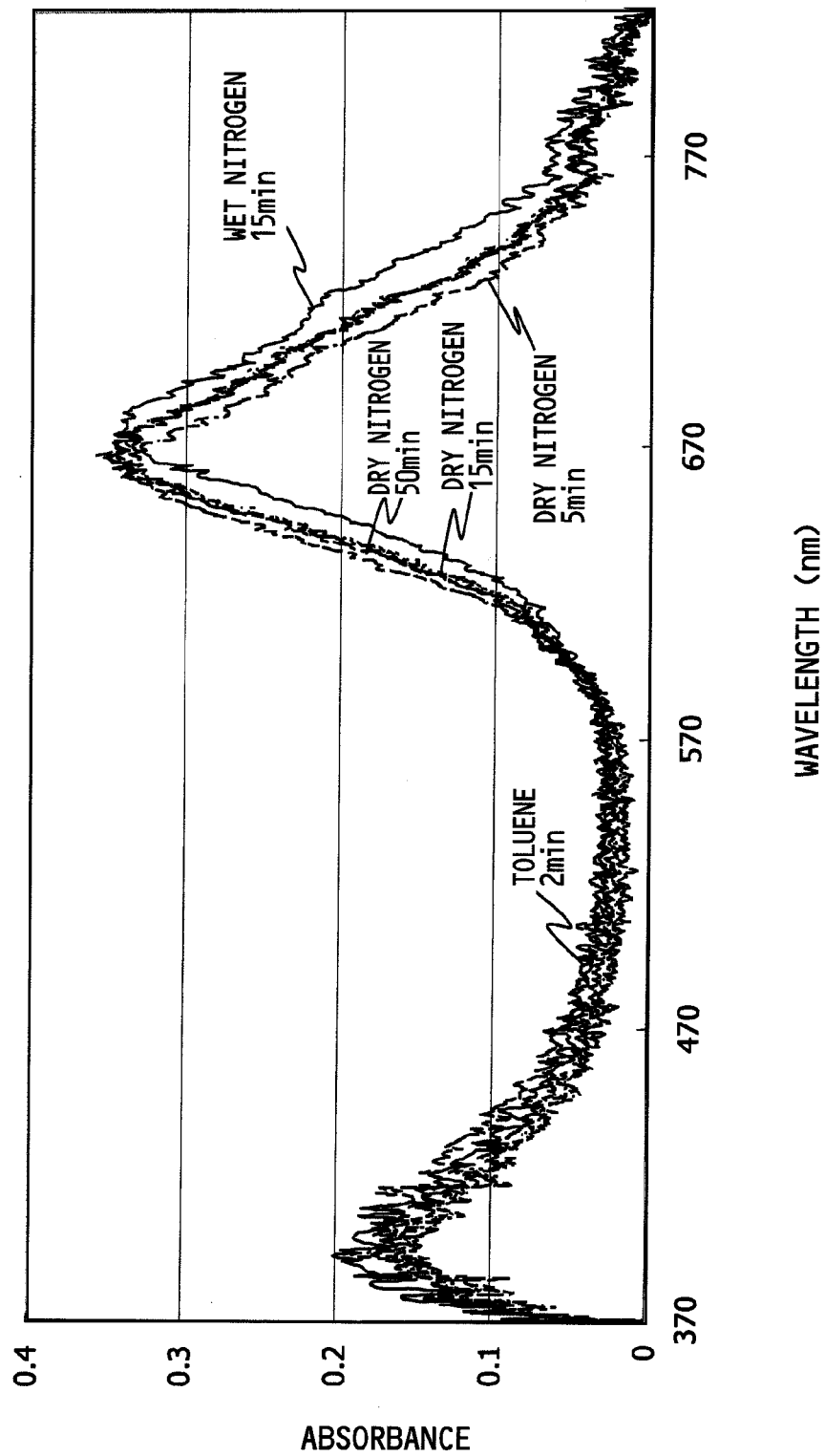
FIG. 13 shows absorption spectra measured by introducing different gases into a detection device using an SPR sensor produced in Example 3.
Figure 14:
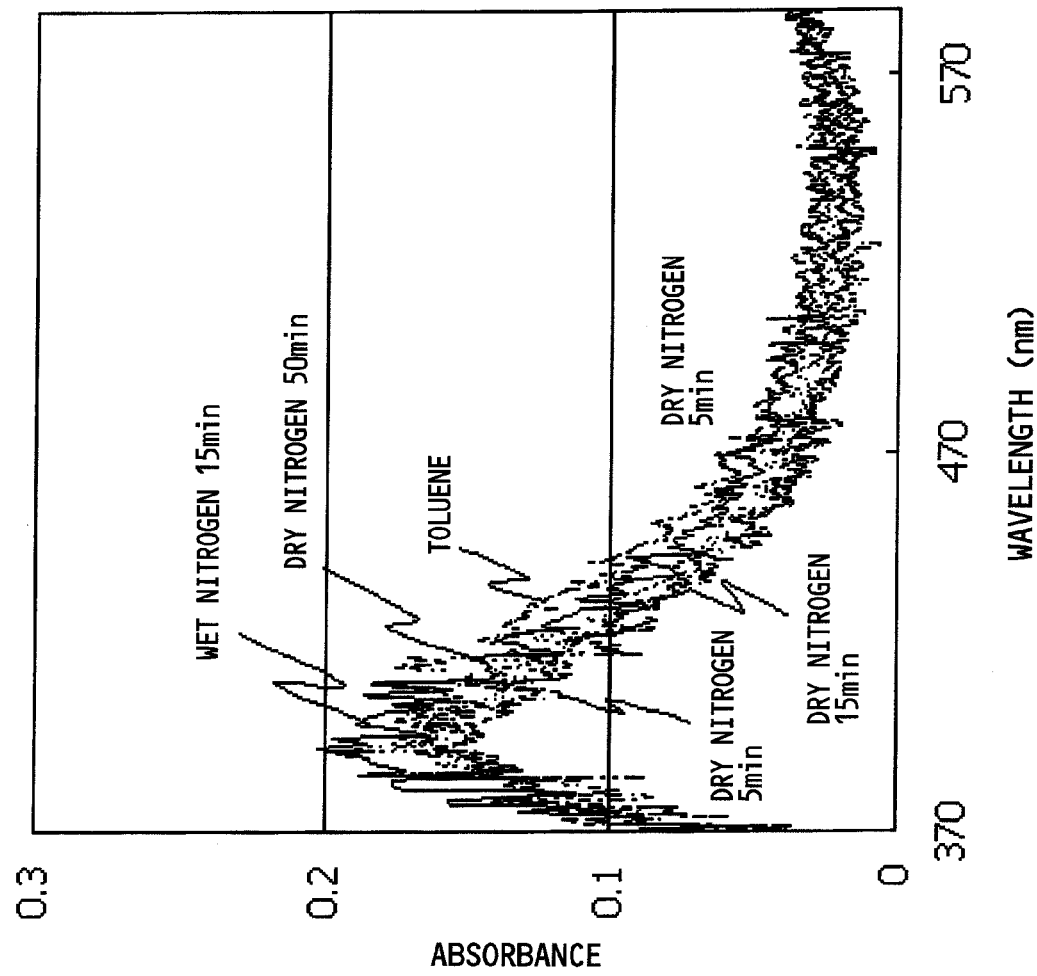
FIG. 14 is an enlarged view of the absorption spectra shown in FIG. 13, which shows absorption peaks on the short-wavelength side.

Then, a detection device such as one shown in FIG. 2 was produced in the same manner as in Example 1. Then, dry nitrogen passed through silica gel, wet nitrogen obtained by bubbling nitrogen in pure water, and toluene-nitrogen obtained by bubbling nitrogen in toluene were introduced as gases to be detected into the detection device one after another. More specifically, dry nitrogen was introduced for 5 minutes, and then wet nitrogen was introduced for 15 minutes, and then dry nitrogen was introduced for 15 minutes, and then toluene-nitrogen was introduced for 2 minutes, and then dry nitrogen was introduced for 50 minutes. FIG. 13 shows absorption spectra obtained in the same manner as in Example 1. FIG. 14 is an enlarged view of the absorption spectra shown in FIG. 13, which shows absorption peaks that appear on the short-wavelength side. In FIGS. 13 and 14, the absorption peaks on the short-wavelength side are due to surface plasmon excited at the region where the film of the mixture of PVK and octadecane is laminated on the metal layer and the absorption peaks on the long-wavelength side are due to surface plasmon excited at the region where the $MgF_2$ layer and the PVA layer are laminated on the metal layer. As can be seen from FIGS. 13 and 14, the absorption peaks on the short-wavelength side and the absorption peaks on the long-wavelength side show different responses. More specifically, the absorption peaks on the long-wavelength side strongly respond to humidity due to strong moisture absorbency of PVA, and therefore the peak wavelength is shifted to the long-wavelength side by introducing wet nitrogen and returned to the initial level by introducing dry nitrogen. Further, the absorption peaks on the long-wavelength side are poorly responsive to toluene. On the other hand, the absorption peaks on the short-wavelength side are less responsive to humidity than PVA due to weak moisture absorbency of the film of the mixture of PVK and octadecane. However, the film of the mixture adsorbs toluene, and therefore the peak wavelength is shifted to the long-wavelength side by exposure to toluene vapor, but is returned to the initial level by introducing dry nitrogen. As can be seen from the results, the use of different sensitive layers makes it possible to observe their different responses to various gases.

Example 4

Metal layers were formed in two regions on a slide glass in the same manner as in Example 1. Then, a 6 mg/mL PMMA solution (solvent: acetone) was applied onto one-half of the surface of one of the two metal layers by a dip coating method to form a 65-nm-thick dielectric constant regulation layer (sensitive layer). On the other hand, a 100-nm-thick $MgF_2$ layer was formed by vacuum vapor deposition on one-half of the surface of the other metal layer, and then a 10 mg/mL PVA solution (solvent: pure water) was applied onto the $MgF_2$ layer by a dip coating method to form a 60-nm-thick PVA layer (sensitive layer) so that a dielectric constant regulation layer composed of the $MgF_2$ layer and the PVA layer was formed.

Figure 15:
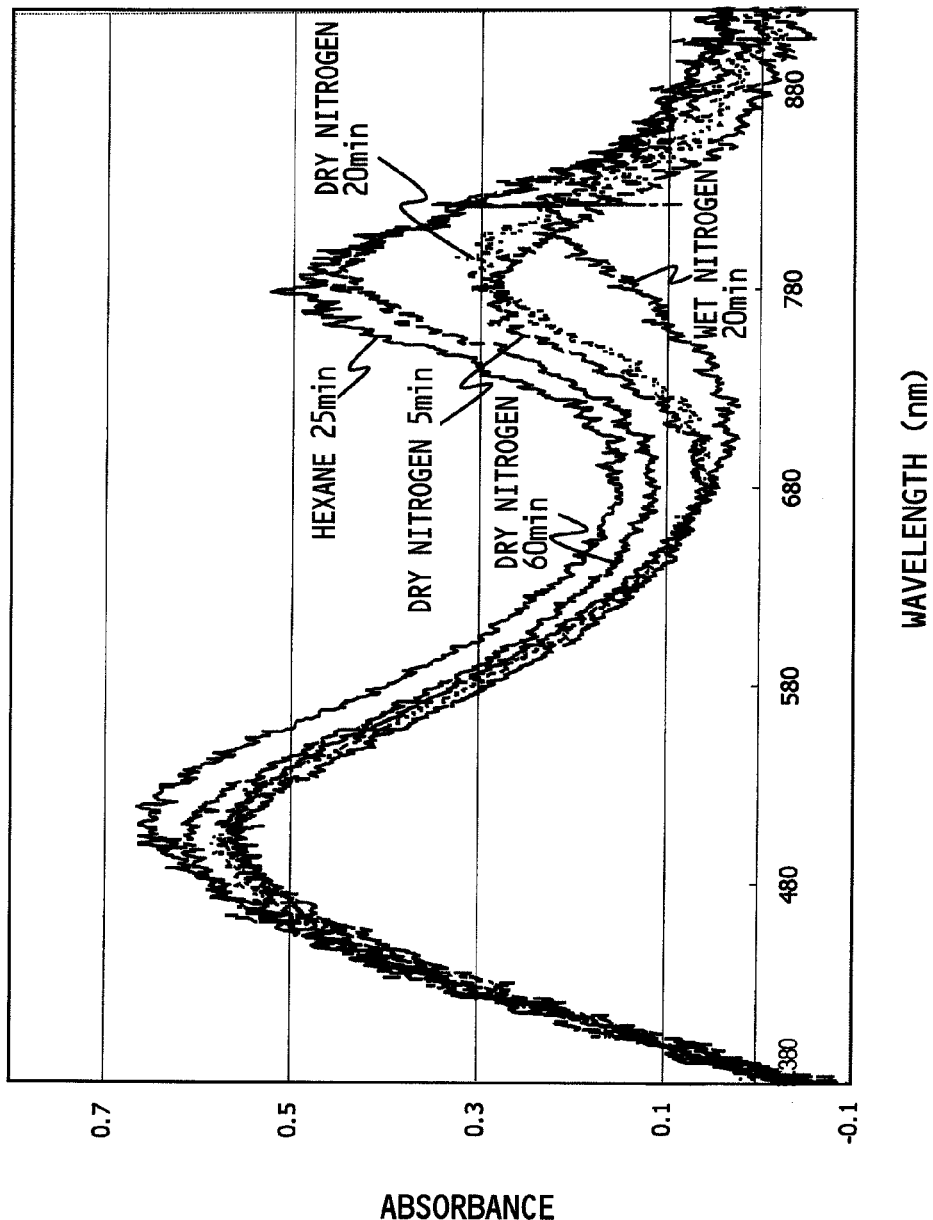
FIG. 15 shows absorption spectra measured by introducing different gases into a detection device using an SPR sensor produced in Example 4.

Then, a detection device such as one shown in FIG. 2 was produced in the same manner as in Example 1. Then, dry nitrogen passed through silica gel, wet nitrogen obtained by bubbling nitrogen in pure water, and hexane-nitrogen obtained by bubbling nitrogen in hexane were introduced as gases to be detected into the detection device one after another. More specifically, dry nitrogen was introduced for 5 minutes, and then wet nitrogen was introduced for 20 minutes, and then dry nitrogen was introduced for 20 minutes, and then hexane-nitrogen was introduced for 25 minutes, and then dry nitrogen was introduced for 60 minutes. FIG. 15 shows absorption spectra obtained in the same manner as in Example 1. In FIG. 15, the absorption peaks on the short-wavelength side are due to surface plasmon excited at the region where the PMMA layer is laminated on the metal layer and the absorption peaks on the long-wavelength side are due to surface plasmon excited at the region where the $MgF_2$ layer and the PVA layer are laminated on the metal layer. As can be seen from FIG. 15, the absorption peaks on the short-wavelength side and the absorption peaks on the long-wavelength side show different responses. More specifically, the absorption peaks on the long-wavelength side strongly respond to humidity due to strong moisture absorbency of PVA, and therefore the peak wavelength is shifted to the long-wavelength side by introducing wet nitrogen and returned to the initial level by introducing dry nitrogen. Further, the absorption peaks on the long-wavelength side are poorly responsive to hexane. On the other hand, the absorption peaks on the short-wavelength side are less responsive to humidity than PVA due to weak moisture absorbency of PMMA. However, PMMA adsorbs hexane, and therefore the peak wavelength is shifted to the long-wavelength side by exposure to hexane vapor, but is returned to the initial level by introducing dry nitrogen. As can be seen from the results, the use of different sensitive layers makes it possible to observe their different responses to various gases.

Example 5

An SPR sensor of Example 5 includes three detection regions. An SPR sensor 110 shown in FIG. 18 includes a transparent substrate 112 and three detection regions provided on the transparent substrate 112. Each of the detection regions is provided by laminating a dielectric constant regulation layer 116A, 116B, or 116C on a metal layer 114. The dielectric constant regulation layers 116A, 116B, and 116C are allowed to have different thicknesses to regulate their dielectric constants so that the three detection regions have different surface plasmon resonances. Such an SPR sensor was produced in the following manner, and was used to detect objects to be detected.

Figure 18:
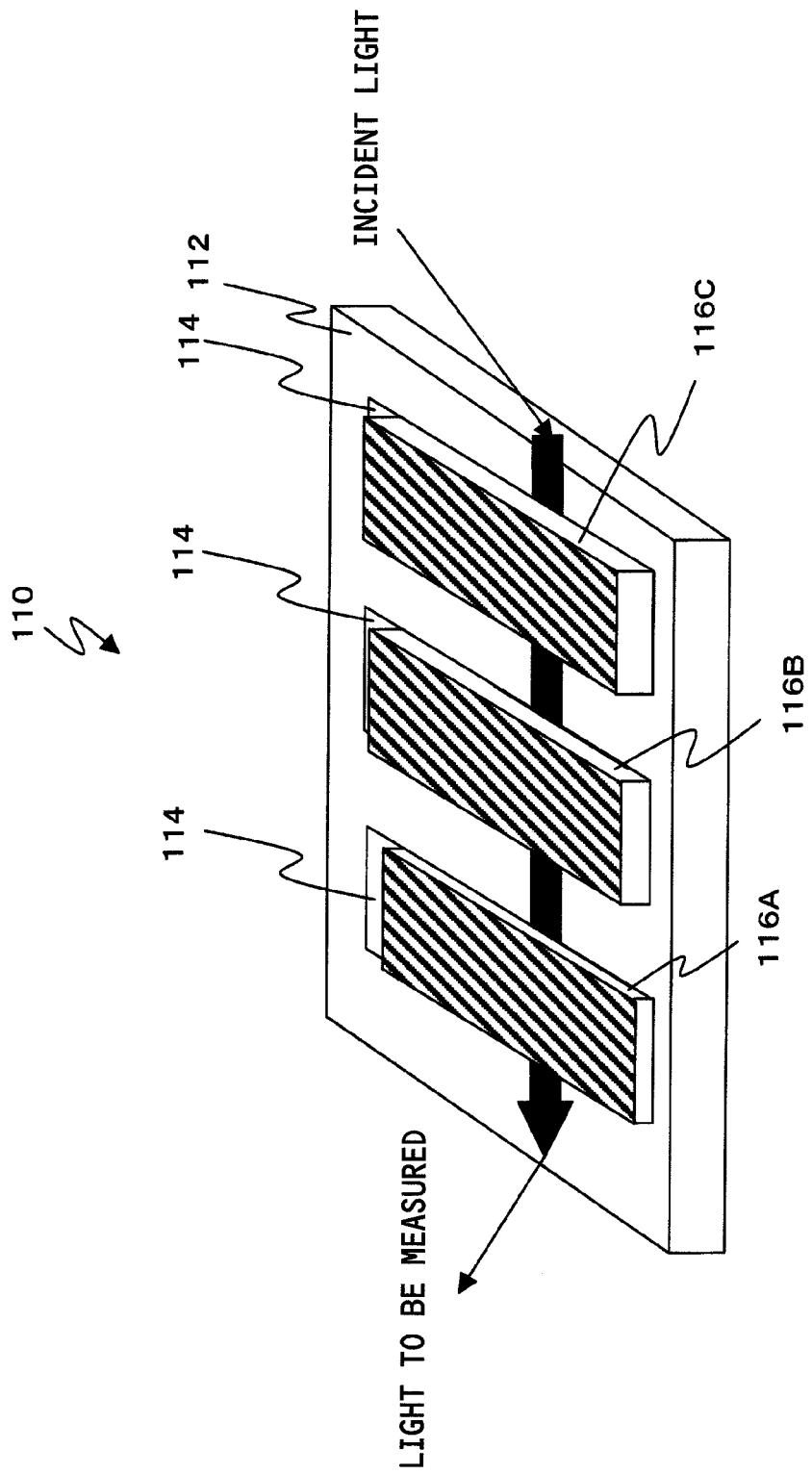
FIG. 18 is a schematic perspective view of another example of the SPR sensor according to the present invention in which three detections regions are provided by laminating, on metal layers, dielectric constant regulation layers made of the same material but having different thicknesses.

First, metal layers were formed at three positions on a slide glass in the same manner as in Example 1 (see FIG. 18). Then, a 5 mg/mL polyvinyl alcohol (PVA) aqueous solution, a 20 mg/mL polyvinyl alcohol aqueous solution, and a 35 mg/mL polyvinyl alcohol aqueous solution were applied by a spin coating method onto the three metal layers, respectively to form PVA layers (sensitive layers) with thicknesses of 22 nm, 58 nm, and 94 nm as dielectric constant regulation layers.

Figure 19:
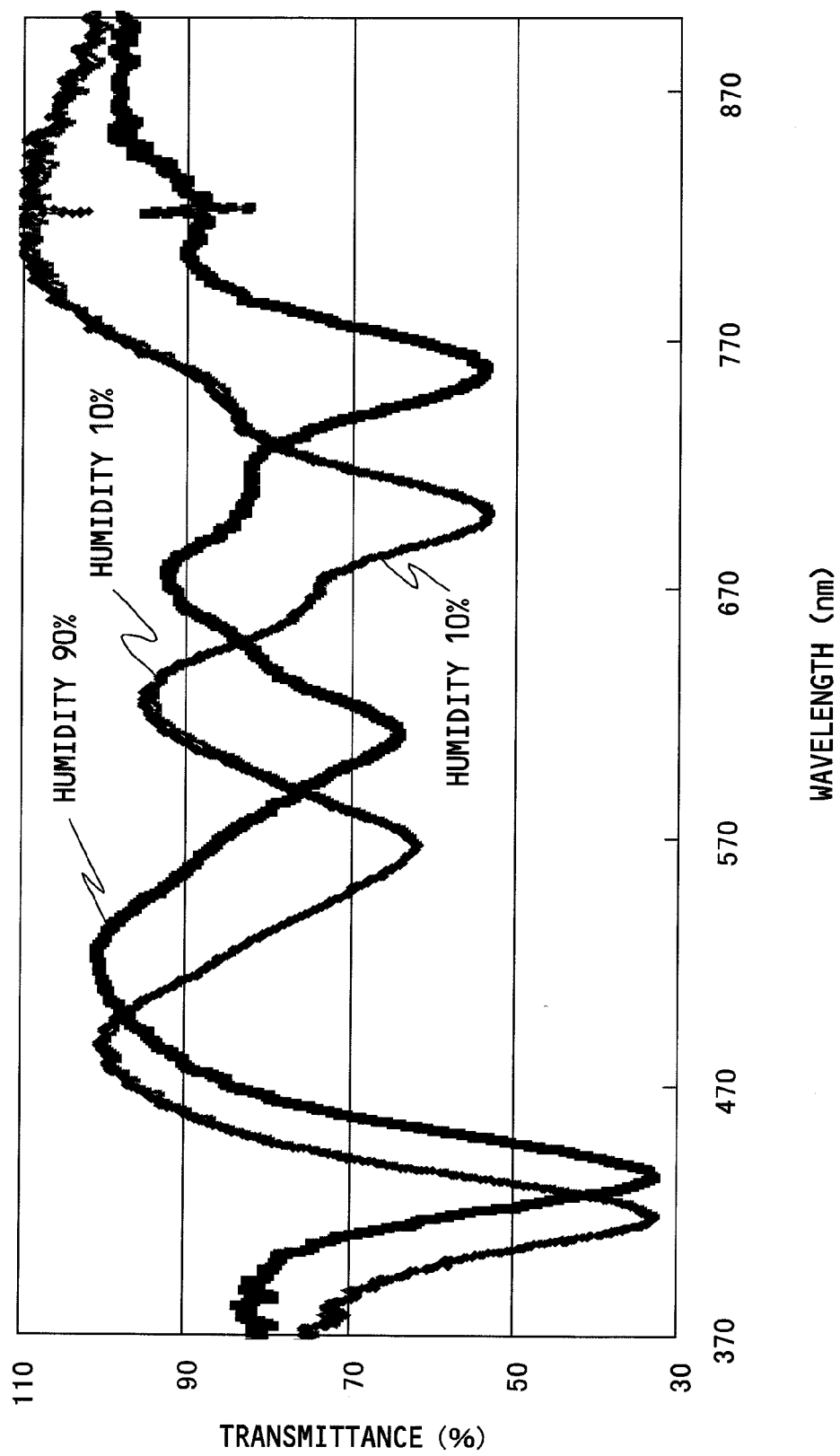
FIG. 19 shows transmittance spectra measured by introducing different gases into a detection device using an SPR sensor produced in Example 5.

Then, a detection device such as one shown in FIG. 2 was produced in the same manner as in Example 1. Then, nitrogen with a humidity of 10% and wet nitrogen with a humidity of 90% obtained by bubbling nitrogen in pure water were introduced as gases to be detected into the detection device alternately. More specifically, nitrogen with a humidity of 10% was introduced for 20 minutes, and then wet nitrogen with a humidity of 90% was introduced for 60 minutes, and then nitrogen with a humidity of 10% was introduced for 10 minutes. FIG. 19 shows transmittance spectra obtained by measuring transmitted light of an s-polarized wave (light having an electric field component perpendicular to the plane of paper) used as reference light and transmitted light of a p-polarized wave (light having an electric field component parallel to the plane of paper) propagating through the same optical path. Unlike Examples 1 to 3, measurement results are shown as transmittance spectra, and therefore absorption caused by surface plasmon is seen as a dip (but from the viewpoint of absorption, it is a peak). In FIG. 19, the dips on the short-wavelength side are due to surface plasmon excited at the PVA layer having a thickness of 22 nm, the dips in the middle-wavelength range, which are next to the dips on the short-wavelength side, are due to surface plasmon excited at the PVA layer having a thickness of 58 nm, and the dips on the long-wavelength side are due to surface plasmon excited at the PVA layer having a thickness of 94 nm. Further, in FIG. 19, the spectra obtained by detecting nitrogen with a humidity of 10% are denoted as "humidity 10%" and the spectrum obtained by detecting nitrogen with a humidity of 90% obtained by bubbling nitrogen in pure water is denoted as "humidity 90%". Even in such a case where three detection regions are provided on one optical path, an object to be detected present on the three detection regions can be simultaneously detected. As can be seen from FIG. 19, the amount of wavelength shift of the dip due to humidity change increases in the order of the short-wavelength side, the middle-wavelength range, and the long-wavelength side. The reason for this can be estimated that the thickness of the dielectric constant regulation layer increases in the order of the short-wavelength side, the middle-wavelength range, and the long-wavelength side, and therefore surface plasmon resonance conditions significantly vary because the volume of water that penetrates into the dielectric constant regulation layer increases as the thickness of the dielectric constant regulation layer increase.

Figure 20:
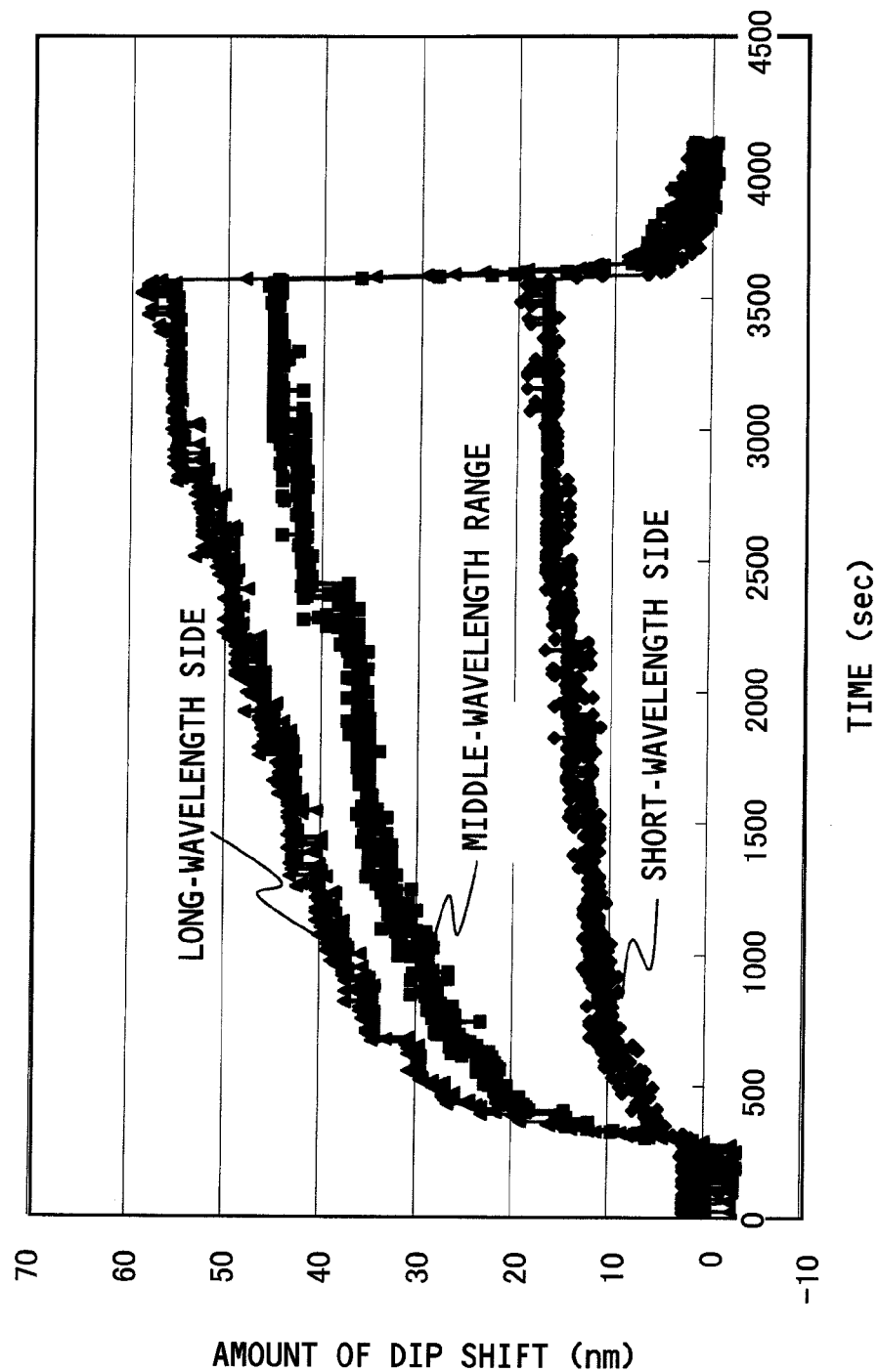
FIG. 20 is a graph showing the amount of wavelength shift versus time of each of a dip on the short-wavelength side, a dip in the middle-wavelength range, and a dip on the long-wavelength side measured using the detection device produced in Example 5.

As described above, the dip wavelength of each of the dip on the short-wavelength side, the dip in the middle-wavelength range, and the dip on the long-wavelength side shifts due to humidity change. FIG. 20 is a graph showing the amount of wavelength shift versus time of each of the dip on the short-wavelength side, the dip in the middle-wavelength range, and the dip on the long-wavelength side.

Figure 21:
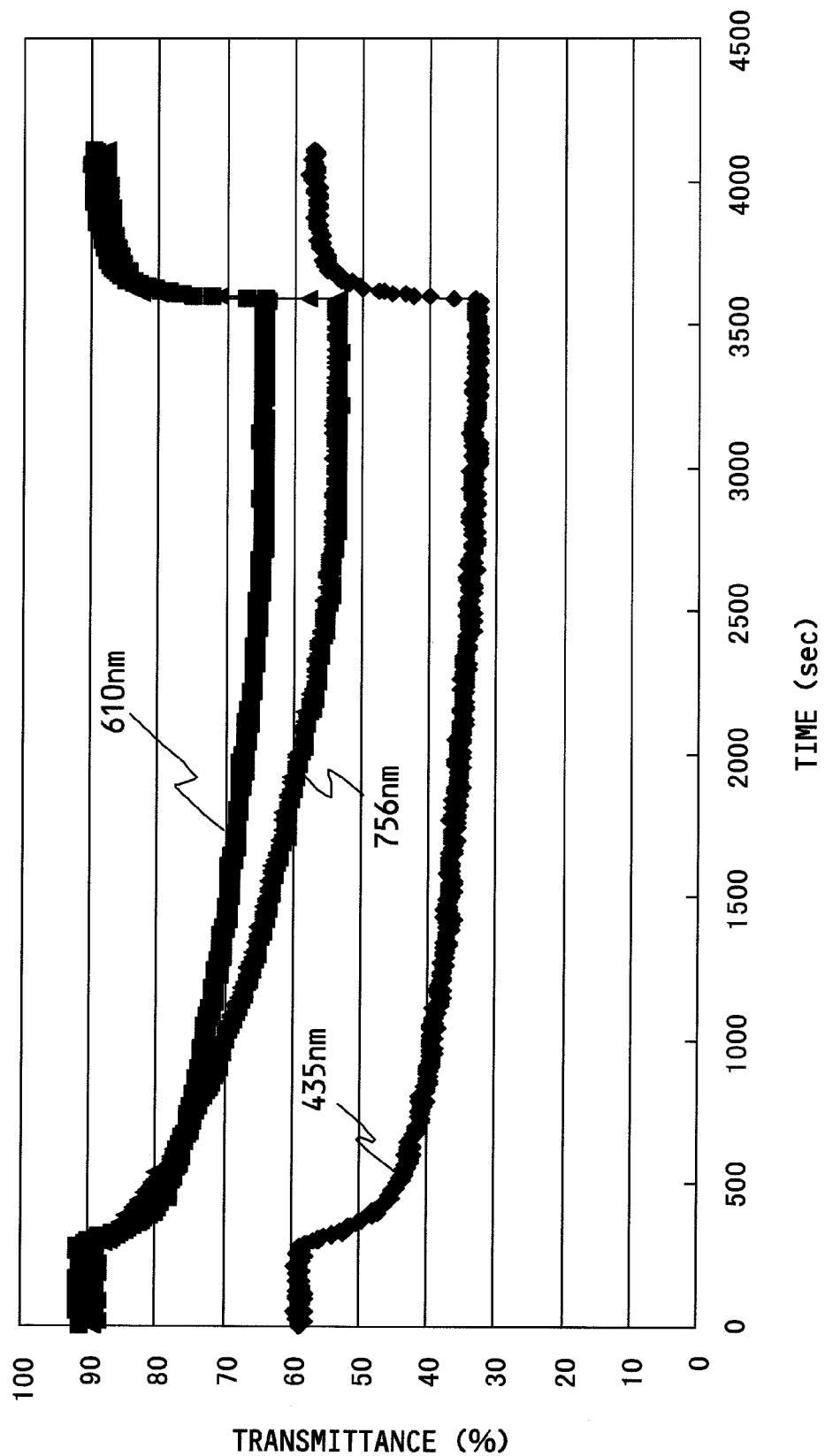
FIG. 21 is a graph showing a temporal change in the transmittance of detection light with a transmittance dip wavelength through each of the dielectric constant regulation layers measured from just before the start of introduction of wet nitrogen into the detection device produced in Example 5 to just after the end of the introduction.

Hereinafter, different responses of the dielectric constant regulation layers of the SPR sensor of Example 5 which are different in the thickness of the PVA layer will be described. FIG. 21 shows a temporal change in the transmittance of detection light (with a transmittance dip wavelength) through each of the dielectric constant regulation layers measured from just before the start of introduction of wet nitrogen with a humidity of 90% to just after the end of the introduction. In other words, FIG. 21 shows a temporal change in transmittance from just before the start of 60-minute introduction of wet nitrogen with a humidity of 90% to just after the end of the introduction measured by allowing detection light of 435 nm that was the transmittance dip wavelength (at the time of moisture absorption) of the PVA layer having a thickness of 22 nm, detection light of 610 nm that was the transmittance dip wavelength (at the time of moisture absorption) of the PVA layer having a thickness of 58 nm, and detection light of 756 nm that was the transmittance dip wavelength (at the time of moisture absorption) of the PVA layer having a thickness of 94 nm to enter the optical path.

Figure 22:
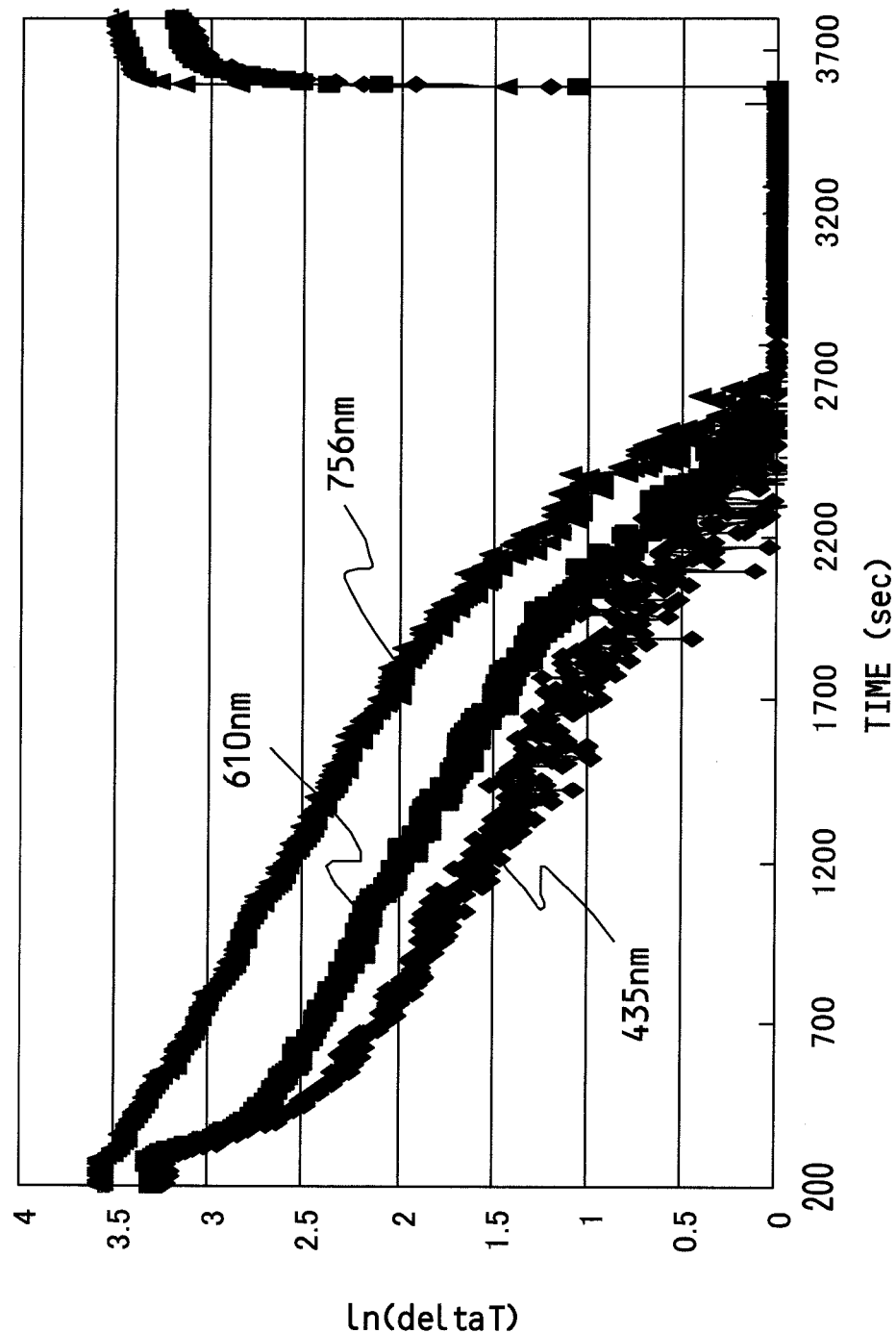
FIG. 22 is a graph obtained by plotting the natural logarithm of transmittance changes (delta T) of detection light of different wavelengths shown in FIG. 21.

FIG. 22 is a graph obtained by plotting the natural logarithm of transmittance changes (delta T) of detection light of wavelengths 435 nm, 610 nm, and 756 nm shown in FIG. 21. As can be seen from FIG. 22, the PVA layers different in thickness show different responses.

Table 1 shows time constants for adsorption/desorption processes calculated from the slopes of the graph shown in FIG. 22. Assuming that the transmittance change is proportional to $e^{-t/\tau}$ where t is time, the time constant is $\tau$ and means the time required for the amount of change in adsorption/desorption process to reach about 65%. When adsorption is not a single process, there is a case where two or more time constants are observed. More specifically, when the value of transmittance (%) is defined as T and its saturation value is defined as Tsat (when the transmittance decreases, the minimum value of the transmittance is used as data), ln(T−Tsat) plotted against time t(s) (horizontal axis) is approximated with one straight line or multiple straight lines (when two or more time constants are observed), and the reciprocal of the slope of the straight line is given as a time constant. At this time, when T−Tsat is defined as $\Delta T$ and the initial value of $\Delta T$ is expressed as $\Delta Tini=Tini-Tsat$, $\Delta T=\Delta Tini \exp[-t/\tau]$ is calculated. It is to be noted that whether the sign in $\exp[-t/\tau]$ is plus or minus depends on which of the absorption and desorption processes occurs, but is defined so that the time constant becomes positive.

In this example, in the case of the adsorption process, the transmittance measured in a stable state after dry nitrogen was sprayed (i.e., in a state where equilibrium adsorption of dry nitrogen with a humidity of 10% was achieved) was defined as Tini and the transmittance measured in a stable state after wet nitrogen was sprayed (i.e., in a state where equilibrium adsorption of wet nitrogen with a humidity of 90% was achieved) was defined as Tsat to calculate τ using the above formula. On the other hand, in the case of the desorption process, τ was calculated in the same manner as in the adsorption process except that the transmittance measured in a stable state after wet nitrogen with a humidity of 90% was sprayed was defined as Tini and the transmittance measured in a stable state after dry nitrogen with a humidity of 10% was sprayed was defined as Tsat.

TABLE 1

| PVA film thickness | Wavelength | Time constant (sec) | | |
|---|---|---|---|---|
| | | Adsorption (A) | Adsorption (B) | Desorption (C) |
| 22 nm | 435 nm | 170 | 1030 | 41 |
| 58 nm | 610 nm | 160 | 1050 | 45 |
| 94 nm | 756 nm | 221 | 1020 | 12 |

As can be seen from Table 1, in the case of adsorption, in each of the channels, an (fast) adsorption process (process A: around 310 to 340 sec) with a small time constant is first observed, and then a (slow) adsorption process (process B: around 700 to 1500 sec) with a large time constant is observed. It can be considered that the fast adsorption process corresponds to adsorption of water molecules to the surface of the PVA film and the slow adsorption process corresponds to penetration of water molecules into the inside of the PVA film, but when the thickness of the PVA film is small, the fast adsorption process is observed for a long period of time. The reason for this can be considered that when the thickness of the PVA film is small, the volume of water that penetrates into the inside of the PVA film is small, and therefore contribution of adsorption of water molecules to the surface of the PVA film to excitation of surface plasmon is large. On the other hand, it can be estimated that when the thickness of the PVA film is large, the effect of penetration of water molecules into the inside of the PVA film is large. In the desorption process (process C: around 3600 sec), each of the channels shows a very fast response, that is, shows a behavior different from that in the adsorption process.

Example 6

Figure 23:
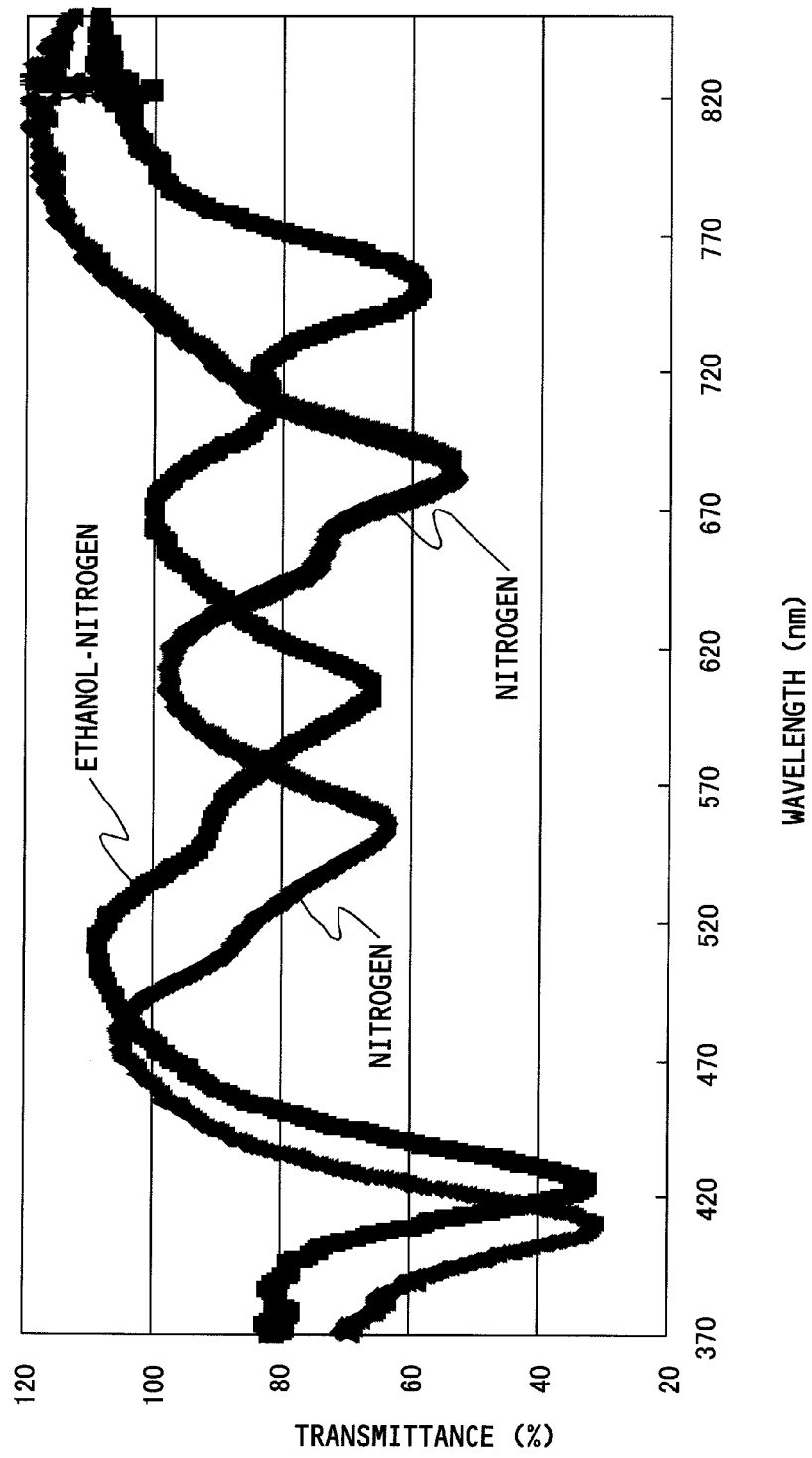
FIG. 23 shows transmittance spectra measured by introducing different gases into a detection device using an SPR sensor produced in Example 6.
Figure 24:
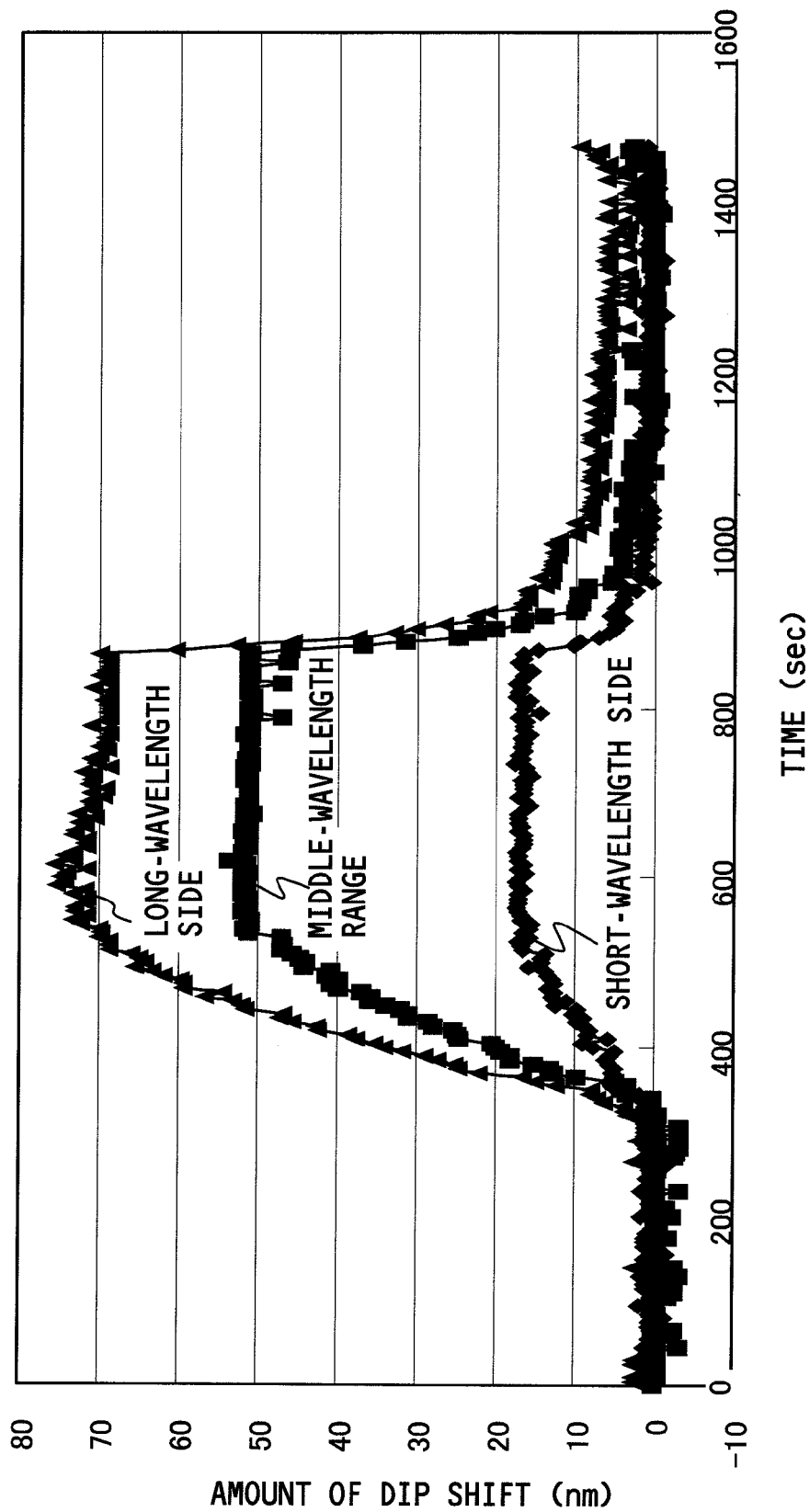
FIG. 24 is a graph showing the amount of wavelength shift versus time of each of a dip on the short-wavelength side, a dip in the middle-wavelength range, and a dip on the long-wavelength side measured using the detection device produced in Example 6.

Detection was performed in the same manner as in Example 5 except that 60-minute introduction of wet nitrogen was changed to 10-minute introduction of ethanol-nitrogen obtained by bubbling nitrogen in ethanol. The thus obtained transmittance spectra are shown in FIG. 23. FIG. 24 is a graph showing the amount of wavelength shift versus time of each of a dip on the short-wavelength side, a dip in the middle-wavelength range, and a dip on the long-wavelength side.

Figure 25:
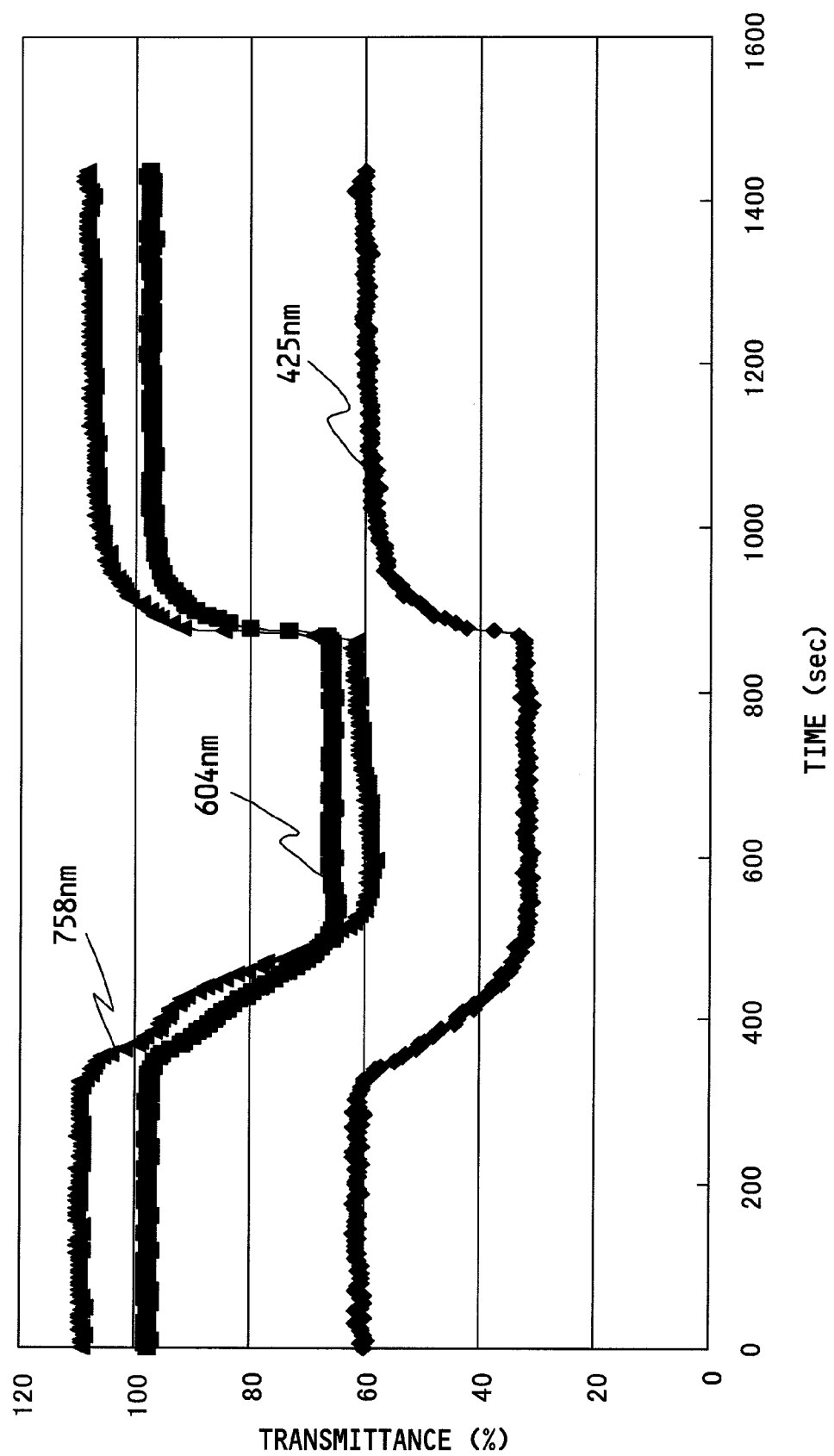
FIG. 25 is a graph showing a temporal change in the transmittance of detection light with a transmittance dip wavelength through each of the dielectric constant regulation layers measured from just before the start of introduction of ethanol-nitrogen into the detection device produced in Example 6 to just after the end of the introduction.
Figure 26:
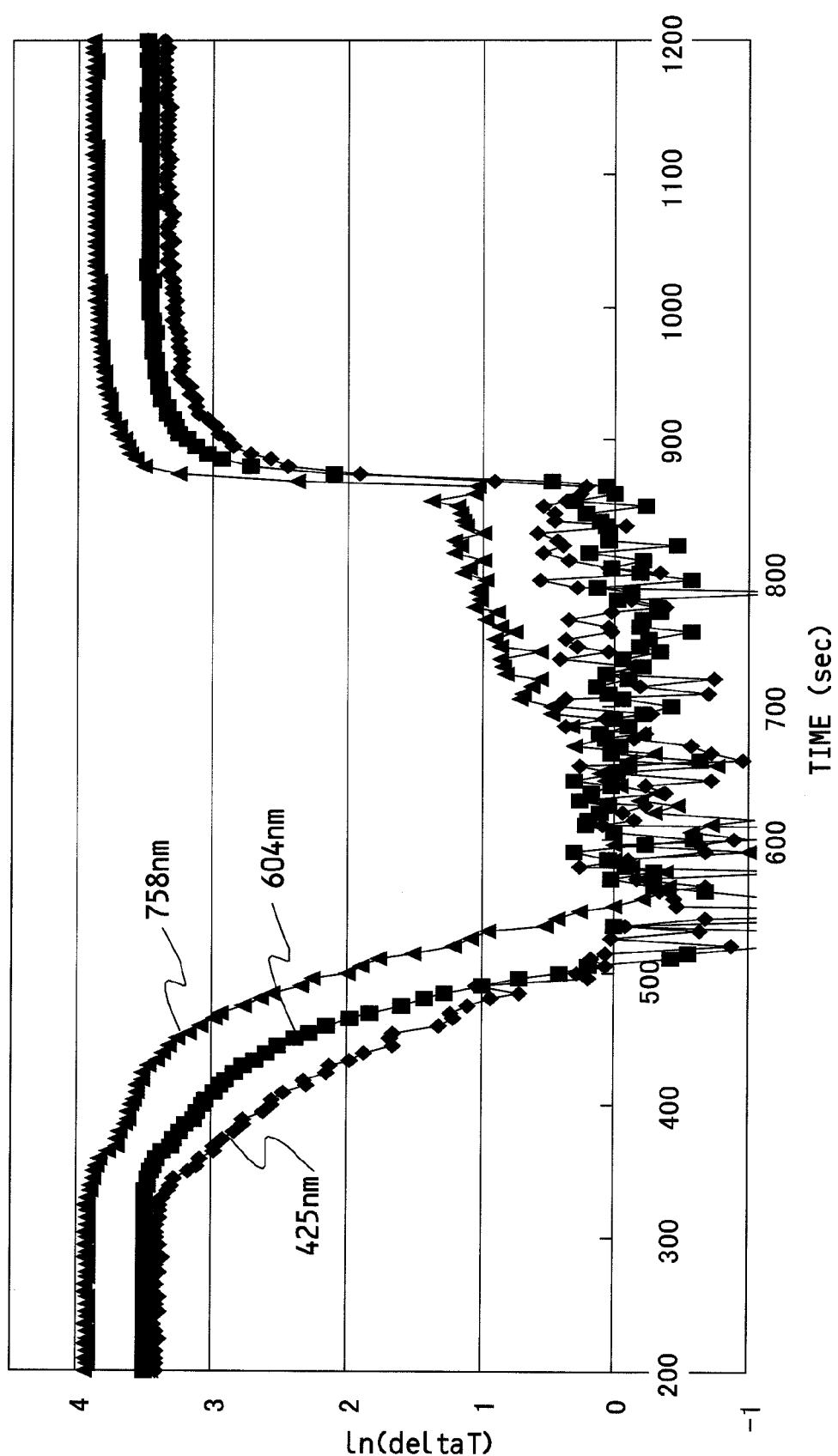
FIG. 26 is a graph obtained by plotting the natural logarithm of transmittance changes (delta T) of detection light of different wavelengths shown in FIG. 25.

FIG. 25 is a graph showing a temporal change in the transmittance of detection light (with a transmittance dip wavelength) through each of the dielectric constant regulation layers measured from just before the start of introduction of ethanol-nitrogen to just after the end of the introduction. FIG. 26 is a graph obtained by plotting the natural logarithm of the transmittance changes (delta T) shown in FIG. 25. As can be seen from FIGS. 25 and 26, the three PVA layers different in thickness which function as sensitive layers are responsive to ethanol, and therefore ethanol can be detected. Table 2 shows time constants for adsorption and desorption processes measured in this example.

TABLE 2

| PVA film thickness | Wavelength | Time constant (sec) | | | |
|---|---|---|---|---|---|
| | | Adsorption (A) | Adsorption (B) | Desorption (C) | Desorption (D) |
| 22 nm | 425 nm | 85 | 45 | 6.5 | 110 |
| 58 nm | 604 nm | 120 | 25 | 5.2 | 220 |
| 94 nm | 758 nm | 208 | 25 | 4.5 | 210 |

As can be seen from Table 2, in the case of adsorption of ethanol vapor, an (slow) adsorption process with a large time constant (process A: around 380 sec) is first observed, and then an (fast) adsorption process with a small time constant (process B: around 470 sec (in the case of film thicknesses of 22 and 58 nm), around 510 sec (in the case of film thickness of 94 nm)) is observed. This result indicates that a fast adsorption/diffusion process and a slow adsorption/diffusion process can be measured by each of the channels by allowing the sensitive layers to have different thicknesses. That is, it is possible to obtain detected data of a fast process and a slow process over a wide dynamic range from measured data of one optical path. Further, in the case of desorption, two components with different time constants are observed (process C: around 870 seconds, process D: around 910 seconds). As has been described above, the SPR sensor according to the present invention having the structure shown in FIG. 18 can easily measure the difference in time constant between different vapors to be adsorbed or the difference in response between sensitive layers having different thicknesses. By previously determining such a difference, it is possible to identify adsorbed chemical species.

Example 7

Figure 27:
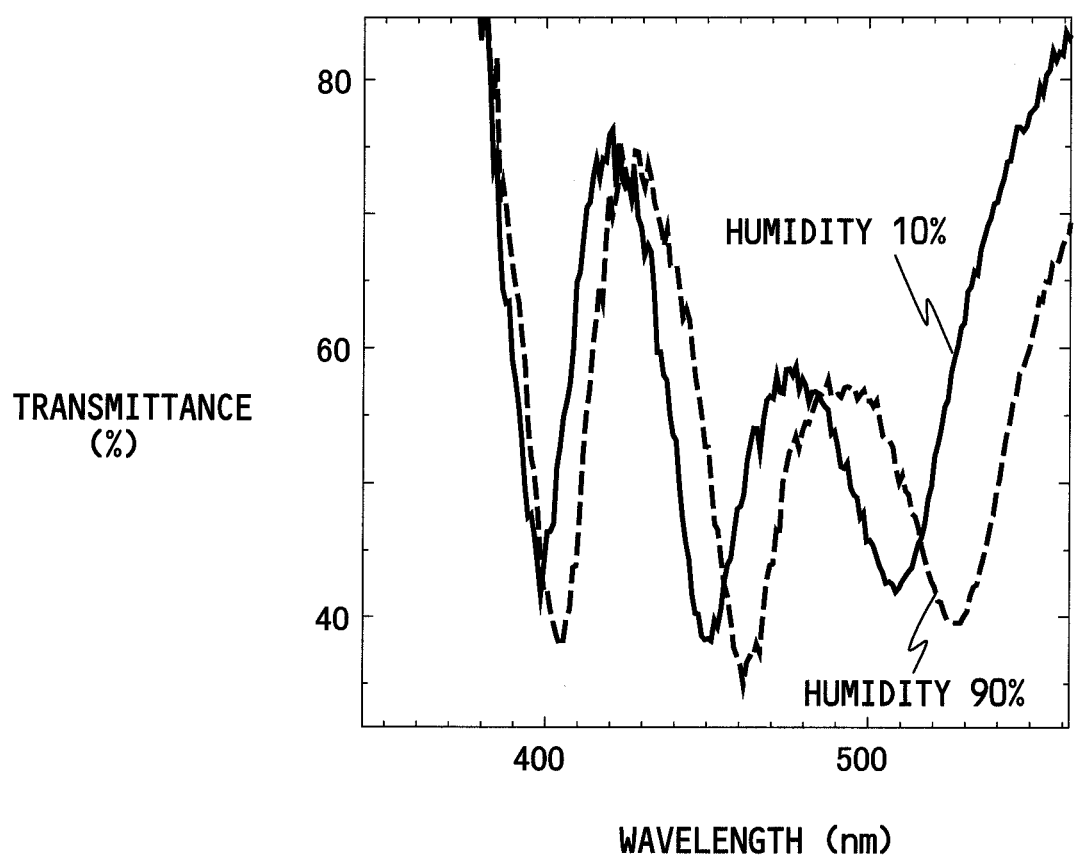
FIG. 27 shows transmittance spectra measured by introducing different gases into a detection device using an SPR sensor produced in Example 7.

Detection was performed in the same manner as in Example 5 except that dielectric constant regulation layers composed of PVA layers (sensitive layers) with thicknesses of 22, 34, and 48 nm were provided. The thus obtained transmittance spectra are shown in FIG. 27. As can be seen also from FIG. 27, even when three detection regions are provided on one optical path, an object to be detected present on the three detection regions can be simultaneously detected.

| DESCRIPTION OF REFERENCE NUMERALS | |
|---|---|
| 10, 40, 50, 60, 70, 80, 100: | SPR sensors |
| 11: | Slide glass (transparent substrate) |
| 12, 14: | Detection regions |
| 16: | Metal layer |
| 18: | PVK layer (dielectric constant regulation layer) |
| 20: | Metal layer |
| 22: | MgF$_2$ layer (dielectric constant regulation layer) |
| 24: | PVA layer (dielectric constant regulation layer) |
| 30: | Casing |
| 32: | Gas inlet |
| 35: | Gas outlet |

| DESCRIPTION OF REFERENCE NUMERALS | |
|---|---|
| 36: | Light source |
| 38: | Detector |

The invention claimed is:

1. An SPR sensor comprising:
an optical path; and
detection regions provided by laminating, on one side surface or plural side surfaces of the optical path, metal layers formed so as to cause a surface plasmon resonance phenomenon, wherein the detection regions are provided at two or more positions on one optical path, and wherein a dielectric constant regulation layer is further laminated in at least one of the two or more detection regions and a dielectric constant of the dielectric constant regulation layer is regulated so that the two or more detection regions have different surface plasmon resonances, and wherein the dielectric constant regulation layer itself, or a surface thereof, laminated in at least one of the two or more detection regions, functions as a sensitive layer having sensitivity to an object to be detected.

2. The SPR sensor according to claim 1, wherein at least one of the two or more detection regions is composed of only a metal layer formed so as to cause a surface plasmon resonance phenomenon and at least one of the two or more detection regions which is different from the detection region composed of only a metal layer is composed of a metal layer formed so as to cause a surface plasmon resonance phenomenon and a dielectric constant regulation layer, laminated on the metal layer, that itself or a surface thereof functions as a sensitive layer having sensitivity to an object to be detected.

3. The SPR sensor according to claim 1, wherein each of the detection regions is composed of a metal layer formed so as to cause a surface plasmon resonance phenomenon and a dielectric constant regulation layer laminated on the metal layer, wherein the detection regions are provided at two or more positions on one optical path, wherein a dielectric constant of each of the dielectric constant regulation layers laminated in the two or more detection regions is regulated so that the two or more detection regions have different surface plasmon resonances, and wherein the dielectric constant regulation layer itself, or a surface thereof, laminated in at least one of the two or more detection regions, functions as a sensitive layer having sensitivity to an object to be detected.

4. The SPR sensor according to any one of claims 1 to 3, wherein each of the two or more detection regions has a dielectric constant regulation layer laminated therein, and the respective dielectric constant regulation layers themselves, or surfaces thereof, provided in the two or more detection regions, function as sensitive layers having sensitivity to different objects to be detected.

5. The SPR sensor according to any one of claims 1 to 3, wherein each of the two or more detection regions has a dielectric constant regulation layer laminated therein, and the dielectric contact regulation layers themselves, or a surface thereof, provided in the two or more detection regions, are made of different materials, and function as sensitive layers having sensitivity to objects to be detected.

6. The SPR sensor according to any one of claims 1 to 3, wherein a dielectric constant regulation layer that functions as an insensitive layer not having sensitivity to an object to be detected is laminated in at least one of the two or more detection regions which is different from the detection region in which a dielectric constant regulation layer that itself, or a surface thereof, functions as a sensitive layer having sensitivity to an object to be detected is laminated.

7. The SPR sensor according to claim 6, wherein the insensitive layer is made of one material selected from the group consisting of glass films, alkali-free glass films, silicon oxide films, quartz glass films, magnesium fluoride films, alumina films, titania films, silicon nitride films, and ITO films.

8. The SPR sensor according to any one of claims 1 to 3, wherein when detection is performed using an optical path having two or more detection regions, a p-polarization component is used as detection light and an s-polarization component is used as reference light.

9. The SPR sensor according to any one of claims 1 to 3, wherein the dielectric constant regulation layers are different in thickness between the detection regions.

10. The SPR sensor according to any one of claims 1 to 3, wherein the dielectric constant regulation layer is made of a transparent medium.

11. The SPR sensor according to any one of claims 1 to 3, wherein the optical path is located in a transparent substrate.

12. The SPR sensor according to claim 11, wherein the transparent substrate is made of inorganic glass.

13. The SPR sensor according to claim 11, wherein the transparent substrate is made of a polymer.

14. The SPR sensor according to any one of claims 1 to 3, wherein the optical path is part of a core layer of a two-dimensional optical waveguide.

15. The SPR sensor according to any one of claims 1 to 3, wherein the optical path is a core of a three-dimensional optical waveguide.

16. The SPR sensor according to any one of claims 1 to 3, wherein the optical path is a core of an optical fiber.

17. The SPR sensor according to any one of claims 1 to 3, wherein the metal layer is made of at least one metal selected from the group consisting of Au, Ag, Pt, Cu, and Al.

18. The SPR sensor according to any one of claims 1 to 3, wherein the sensitive layer contains a solvent-soluble material as a material having sensitivity.

19. The SPR sensor according to claim 18, wherein the solvent-soluble material is a hydrophilic material.

20. The SPR sensor according to claim 19, wherein the hydrophilic material is at least one selected from the group consisting of polyvinyl alcohol, polyacrylic acid, polystyrene sulfonic acid, polyallylamine, poly(diallyldimethylammonium chloride), polyamide acid, and polyimide precursors.

21. The SPR sensor according to claim 18, wherein the solvent-soluble material is a hydrophobic material.

22. The SPR sensor according to claim 21, wherein the hydrophobic material is polyvinylcarbazole, polymethylmethacrylate, wax, polyimide, or polytetrafluoroethylene.

23. The SPR sensor according to any one of claims 1 to 3, wherein the sensitive layer contains a material having sensitivity with a polymer as a matrix.

24. The SPR sensor according to claim 1, wherein the dielectric constant regulation layer itself functions as a sensitive layer having sensitivity to an object to be detected.

25. The SPR sensor according to any one of claims 1 to 3, wherein at least two of the two or more detection regions have a dielectric constant regulation layer laminated therein, and the dielectric constant regulation layers themselves, or surfaces thereof, provided at the at least two of the two or more detection regions, are made of different materials from each other.

26. The SPR sensor according to claim 25, wherein the dielectric constant regulation layers provided at the at least two of the two or more detection regions, have sensitivity respectively to a hydrophobic material and to a hydrophilic material.

27. The SPR sensor according to claim 25, wherein the metal layers respectively of at least two of the two or more detection regions are made of different metals.

28. The SPR sensor according to claim 1, wherein the dielectric constant regulation layer itself has the ability to absorb an object to be detected, or the surface of the dielectric constant regulation layer has the ability to adsorb or bind to an object to be detected.

* * * * *